(12) United States Patent
Metzger et al.

(10) Patent No.: US 6,413,279 B1
(45) Date of Patent: Jul. 2, 2002

(54) FLOATING BEARING KNEE JOINT PROSTHESIS WITH A FIXED TIBIAL POST

(75) Inventors: Robert Metzger, Walkarusa; David Ray Brown; Troy Hershberger, both of Warsaw; Kevin Cox, Leesburg, all of IN (US)

(73) Assignee: Biomet, Inc., Warsaw, IN (US)

( * ) Notice: Subject to any disclaimer, the term of this patent is extended or adjusted under 35 U.S.C. 154(b) by 0 days.

(21) Appl. No.: 09/695,448

(22) Filed: Oct. 24, 2000

Related U.S. Application Data

(63) Continuation-in-part of application No. 09/259,873, filed on Mar. 1, 1999, now Pat. No. 6,165,223.

(51) Int. Cl.$^7$ ................................................. A61F 2/38
(52) U.S. Cl. .................................. 623/20.29; 623/20.14
(58) Field of Search .......................... 623/20.14, 20.24, 623/20.27, 20.28, 20.29, 20.31

(56) References Cited

U.S. PATENT DOCUMENTS

| | | | |
|---|---|---|---|
| 3,728,742 A | 4/1973 | Averill et al. | |
| 3,748,662 A | 7/1973 | Helfet | |
| 3,774,244 A | 11/1973 | Walker | |
| 3,958,278 A | 5/1976 | Lee et al. | |
| 3,964,106 A | 6/1976 | Hutter, Jr. et al. | |
| 3,996,624 A | 12/1976 | Noiles | |
| 4,081,866 A | 4/1978 | Upshaw et al. | |
| 4,085,466 A | 4/1978 | Goodfellow et al. | |
| 4,094,017 A | 6/1978 | Matthews et al. | |

(List continued on next page.)

FOREIGN PATENT DOCUMENTS

| | | |
|---|---|---|
| DE | 35 29 894 A1 | 3/1987 |
| DE | 40 09 360 A1 | 8/1991 |
| EP | 0 186 471 A3 | 7/1986 |
| EP | 0 327 297 A2 | 8/1989 |
| EP | 0 346 183 A1 | 12/1989 |

(List continued on next page.)

OTHER PUBLICATIONS

"AGC, Total Knee System, Intramedullary with Distractor Surgical Technique," brochure, Biomet, Inc. 1989.
"AGC, Total Knee System, Intramedullary with Distractor Surgical Overview," brochure, Biomet, Inc. 1989.

(List continued on next page.)

*Primary Examiner*—Jeffrey A. Smith
*Assistant Examiner*—Michael B. Priddy
(74) *Attorney, Agent, or Firm*—Harness, Dickey & Pierce, P.L.C.

(57) ABSTRACT

This invention relates to a floating bearing knee joint prosthesis having a fixed tibial post used for replacing the articulating knee portion of a femur and a tibia. The floating bearing knee joint prosthesis includes a femoral component, a tibial component, a guide post and a bearing member. The femoral component includes an engagement member, a first femoral bearing surface and a second femoral bearing surface. The tibial component includes a tibial bearing surface. The guide post extends from the tibial component and is operable to be engaged by the engagement member of the femoral component. The bearing member includes a first bearing surface that articulates with the first femoral bearing surface, a second bearing surface that articulates with the second femoral bearing surface and a third bearing surface that articulates with the tibial bearing surface. The bearing member further includes a posterior lip extension that substantially inhibits the bearing member from dislocating upon flexion of the knee joint prosthesis. The bearing member also defines an opening that receives the guide post where the opening is configured to substantially inhibit rotational movement of the bearing member relative to the tibial component in extension.

20 Claims, 13 Drawing Sheets

U.S. PATENT DOCUMENTS

| | | | |
|---|---|---|---|
| 4,136,405 A | 1/1979 | Pastrick et al. | |
| 4,207,627 A | 6/1980 | Cloutier | |
| 4,209,861 A | 7/1980 | Walker et al. | |
| 4,213,209 A | 7/1980 | Insall et al. | |
| 4,215,439 A | 8/1980 | Gold et al. | |
| 4,216,549 A | 8/1980 | Hillberry et al. | |
| 4,219,893 A | 9/1980 | Noiles | |
| 4,224,696 A | 9/1980 | Murray et al. | |
| 4,224,697 A | 9/1980 | Murray et al. | |
| 4,249,270 A | 2/1981 | Bahler et al. | |
| 4,257,129 A | 3/1981 | Volz | |
| 4,285,070 A | 8/1981 | Averill | |
| 4,298,992 A | 11/1981 | Burstein et al. | |
| 4,301,553 A | 11/1981 | Noiles | |
| 4,309,778 A | 1/1982 | Buechel et al. | |
| 4,340,978 A | 7/1982 | Buechel et al. | |
| 4,462,120 A | 7/1984 | Rambert et al. | |
| 4,470,158 A | 9/1984 | Pappas et al. | |
| 4,538,305 A | 9/1985 | Engelbrecht et al. | |
| 4,568,348 A | 2/1986 | Johnson et al. | |
| 4,586,933 A | 5/1986 | Shoji et al. | |
| 4,634,444 A | 1/1987 | Noiles | |
| 4,637,382 A | 1/1987 | Walker | |
| 4,673,407 A | 6/1987 | Martin | |
| 4,711,639 A | 12/1987 | Grundei | |
| 4,714,474 A | 12/1987 | Brooks, Jr. et al. | |
| 4,728,332 A | 3/1988 | Albrektsson | |
| 4,808,185 A | 2/1989 | Penenberg et al. | |
| 4,822,362 A | 4/1989 | Walker et al. | |
| 4,822,365 A | 4/1989 | Walker et al. | |
| 4,865,607 A | 9/1989 | Witzel et al. | |
| 4,883,488 A | 11/1989 | Bloebaum et al. | |
| 4,888,021 A | 12/1989 | Forte et al. | |
| 4,892,547 A | 1/1990 | Brown | |
| 4,911,721 A | 3/1990 | Branemark et al. | |
| 4,950,297 A | 8/1990 | Elloy et al. | |
| 4,950,298 A | 8/1990 | Gustilo et al. | |
| 4,959,071 A | 9/1990 | Brown et al. | |
| 5,007,933 A | 4/1991 | Sidebotham et al. | |
| 5,011,496 A | 4/1991 | Forte et al. | |
| 5,037,439 A | 8/1991 | Albrektsson et al. | |
| 5,047,057 A | 9/1991 | Lawes | |
| 5,064,437 A | 11/1991 | Stock et al. | |
| 5,071,438 A | 12/1991 | Jones et al. | |
| 5,080,675 A | 1/1992 | Lawes et al. | |
| 5,092,895 A | 3/1992 | Albrektsson et al. | |
| 5,116,375 A | 5/1992 | Hofmann | |
| 5,116,376 A | 5/1992 | May | |
| 5,133,758 A | 7/1992 | Hollister | |
| 5,147,405 A | 9/1992 | Van Zile et al. | |
| 5,147,406 A | 9/1992 | Houston et al. | |
| 5,171,283 A | 12/1992 | Pappas et al. | |
| 5,176,710 A | 1/1993 | Hahn et al. | |
| 5,181,925 A | 1/1993 | Houston et al. | |
| 5,197,987 A | 3/1993 | Koch et al. | |
| 5,219,362 A | 6/1993 | Tuke et al. | |
| 5,226,916 A | 7/1993 | Goodfellow et al. | |
| 5,271,747 A | 12/1993 | Wagner et al. | |
| 5,282,868 A | 2/1994 | Bahler | |
| 5,282,870 A | 2/1994 | Moser et al. | |
| 5,314,482 A | 5/1994 | Goodfellow et al. | |
| 5,314,483 A | 5/1994 | Wehrli et al. | |
| 5,330,532 A | 7/1994 | Ranawat | |
| 5,330,533 A | 7/1994 | Walker | |
| 5,330,534 A | 7/1994 | Herrington et al. | |
| 5,358,527 A | 10/1994 | Forte | |
| 5,358,529 A | 10/1994 | Davidson | |
| 5,358,530 A | 10/1994 | Hodorek | |
| 5,358,531 A | 10/1994 | Goodfellow et al. | |
| 5,370,699 A | 12/1994 | Hood et al. | |
| 5,370,700 A | 12/1994 | Sarkisian et al. | |
| 5,370,701 A | 12/1994 | Finn | |
| 5,387,240 A | 2/1995 | Pottenger et al. | |
| 5,395,401 A | 3/1995 | Bahler | |
| 5,405,395 A | 4/1995 | Coates | |
| 5,413,604 A | 5/1995 | Hodge | |
| 5,413,608 A | 5/1995 | Keller | |
| 5,480,446 A | 1/1996 | Goodfellow et al. | |
| 5,514,183 A | 5/1996 | Epstein et al. | |
| 5,549,686 A | 8/1996 | Johnson et al. | |
| 5,549,689 A | 8/1996 | Epstein et al. | |
| 5,556,432 A | 9/1996 | Kubein-Meesenburg et al. | |
| 5,571,197 A | 11/1996 | Insall | |
| 5,609,639 A | 3/1997 | Walker | |
| 5,609,643 A | 3/1997 | Colleran et al. | |
| 5,609,645 A | 3/1997 | Vinciguerra | |
| 5,639,279 A | 6/1997 | Burkinshaw et al. | |
| 5,658,342 A | 8/1997 | Draganich et al. | |
| 5,658,344 A | 8/1997 | Hurlburt | |
| 5,683,467 A | 11/1997 | Pappas | |
| 5,683,468 A | 11/1997 | Pappas | |
| 5,702,458 A | 12/1997 | Burstein et al. | |
| 5,702,466 A | 12/1997 | Pappas et al. | |
| 5,725,584 A | 3/1998 | Walker et al. | |
| 5,755,801 A | 5/1998 | Walker et al. | |
| 5,755,802 A | 5/1998 | Gerber | |
| 5,755,804 A * | 5/1998 | Schmotzer et al. | 623/20 |
| 5,800,552 A | 9/1998 | Forte | |
| 5,824,096 A | 10/1998 | Pappas et al. | |
| 5,824,100 A | 10/1998 | Kester et al. | |
| 5,824,102 A | 10/1998 | Buscayret | |
| 5,824,103 A | 10/1998 | Williams | |
| 5,871,542 A | 2/1999 | Goodfellow et al. | |
| 5,871,545 A | 2/1999 | Goodfellow et al. | |
| 5,871,546 A | 2/1999 | Colleran et al. | |
| 5,879,392 A | 3/1999 | McMinn | |
| 5,879,394 A | 3/1999 | Ashby et al. | |
| 5,906,643 A | 5/1999 | Walker | |
| 5,997,577 A | 12/1999 | Herrington et al. | |
| 6,004,352 A | 12/1999 | Buni | |
| 6,039,764 A | 3/2000 | Pottenger et al. | |
| 6,068,658 A | 5/2000 | Insall et al. | |
| 6,080,195 A | 6/2000 | Colleran et al. | |
| 6,090,144 A | 7/2000 | Letot et al. | |
| 6,099,570 A * | 8/2000 | Livet et al. | 623/20.21 |
| 6,117,175 A | 9/2000 | Bosredon | |
| 6,123,728 A * | 9/2000 | Brosnahan et al. | 623/20.24 |
| 6,123,729 A | 9/2000 | Insall et al. | |
| 6,152,960 A | 11/2000 | Pappas | |
| 6,162,254 A | 12/2000 | Timoteo | |
| 6,165,223 A * | 12/2000 | Metzger et al. | 623/20.27 |
| 6,203,576 B1 | 3/2001 | Afriat et al. | |
| 6,206,926 B1 * | 3/2001 | Pappas | 623/20.27 |
| 6,210,444 B1 | 4/2001 | Webster et al. | |
| 6,210,445 B1 | 4/2001 | Zawadzki | |
| 6,217,618 B1 | 4/2001 | Hileman | |

FOREIGN PATENT DOCUMENTS

| | | |
|---|---|---|
| EP | 0 349 173 A1 | 1/1990 |
| EP | 0 381 352 A1 | 8/1990 |
| EP | 0 442 330 A2 | 8/1991 |
| EP | 0 519 873 A2 | 6/1992 |
| EP | 0 498 586 A1 | 8/1992 |
| EP | 0 510 178 B1 | 10/1992 |
| EP | 0 510 299 A1 | 10/1992 |
| EP | 0 627 203 A2 | 12/1994 |
| EP | 0 592 750 B1 | 1/1999 |
| EP | 653 927 B1 | 3/2001 |
| GB | 1 534 263 | 11/1978 |
| GB | 2 219 942 A | 12/1989 |
| GB | 2 296 443 A | 7/1996 |

| | | |
|---|---|---|
| GB | 2313314 | 4/2000 |
| WO | WO 92/03108 | 3/1992 |
| WO | WO 92/08424 | 12/1992 |
| WO | WO 94/26212 | 11/1994 |
| WO | WO 96/03097 | 2/1996 |
| WO | WO 96/24311 | 8/1996 |
| WO | WO 98/02116 | 1/1998 |

OTHER PUBLICATIONS

"AGC, Total Knee System, Unicondylar Surgical Overview," brochure, Biomet, Inc. 1989.

"AGC, Total Knee System, Surgical Overview featuring Accu–Line™ Knee Instrumentation," brochure, Biomet, Inc., copyright 1991.

"Controlling the Motion of Total Knee Replacements using Intercondylar Guide Surfaces," Journal of Orthopedic Research, Walker, P. and Sathasivam, S., 2000, pp. 48, 54.

"Stability and Range of Motion of Insall–Burstein Condylar Prostheses", The Journal of Arthroplasty, vol. 10, No. 3 1995., Kocmond, J., Delp, S and Stern, S., pp. 383, 386.

"The Transepicondylar Axis Approximates the Optimal Flexion Axis of the Knee," Clinical Orthopaedics and Related Research, No. 356, Nov. 1998, Churchill, D., Incavo, S., Johnson, C. and Beynnon, B., pp. 111, 117.

"AGC, Total Knee System, Tradition Series," brochure, Biomet, Inc. copyright 1995.

"Interaction Between Active and Passive Knee Stabilizers During Level Walking," O.D. Schipplein and T.P. Andriacchi, Journal of Orthopaedic Research, 1991.

"Maxim, The Complete Knee System," brochure, Biomet, Inc., copyright 1995.

"Performance, The Total Knee System," brochure, Biomet, Inc., copyright 1997.

"The Role of Joint Load in Knee Stability," Keith L. Markolf, PhD, William L. Bargar, M.D., Stephen C. Shoemaker, B.S. and Harlan C. Amstutz, M.D., Journal of Bone and Joint Surgery, Incorporated, copyright 1981.

"Trac Knee System" Design Rationale, Louis F. Draganich, PhD, Lawrency A. Pottenger, M.D., PhD., Nov. 1996.

Aglietti, P., Buzzi, R., and Menchetti, P.P.M., "Total Knee Replacement—Problems Related to the Posterior Cruciate Ligament and Fixed Versus Mobile Bearings," European Federation of National Associations of Orthopaedics and Traumatology, pp. 15–24, undated (1996 or later).

H. Kurosawa, et al., "Geometry and Motion of the Knee for Implant and Orthotic Design," J. Biomechanics, vol. 18, No. 7, pp. 287–499 (1985).

Menchetti, Paolo, M., M.D., Walker, Peter, S. PhD. "Mechanical Evaluation of Mobile Bearing Knees," The American Journal of Knee Surgery, vol. 10, No. 2, Spring 1997, pp. 73–82.

"The Profix Total Knee System," by Smith & Nephew, copyright 1999, 2 sheets.

* cited by examiner

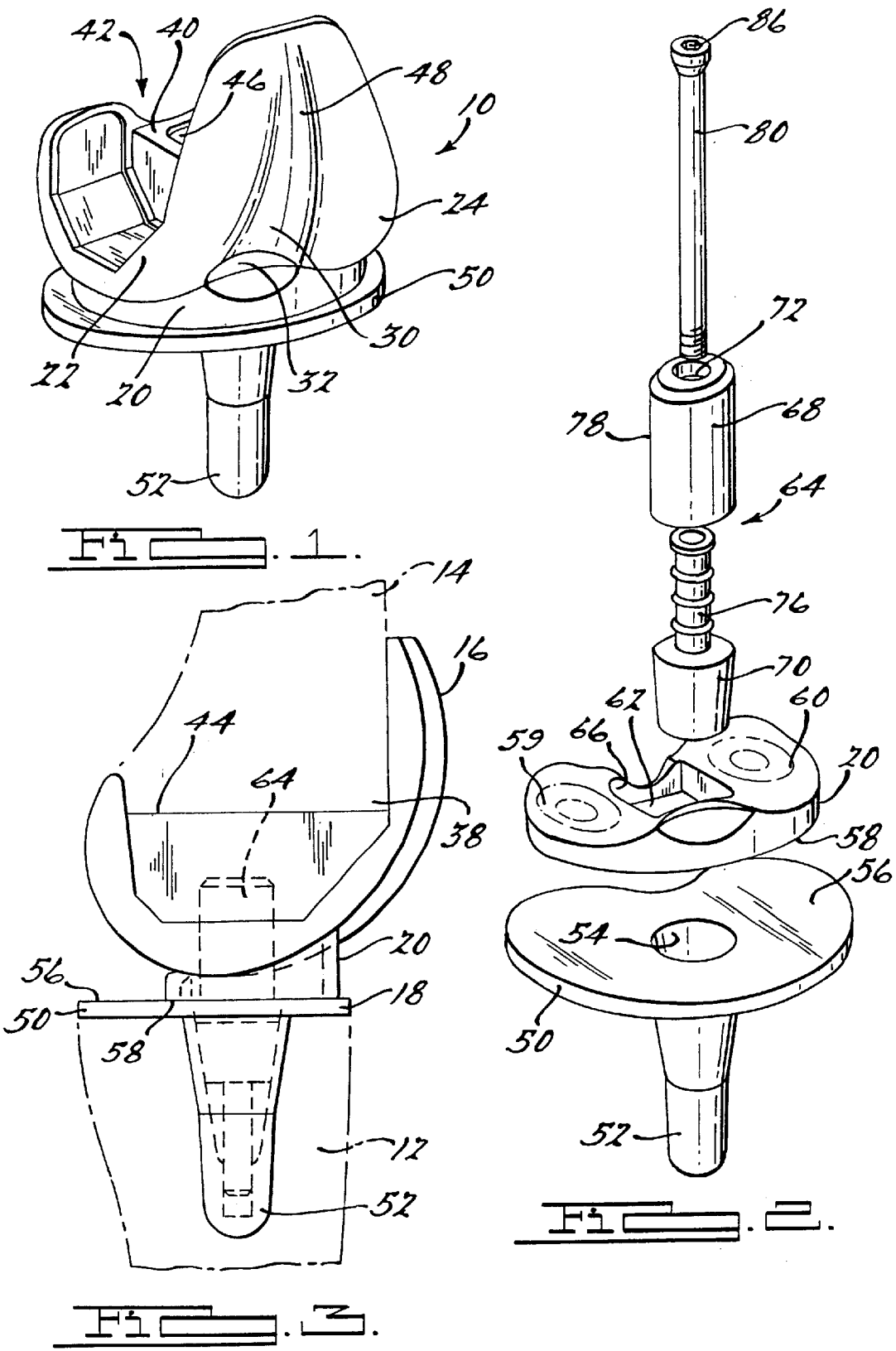

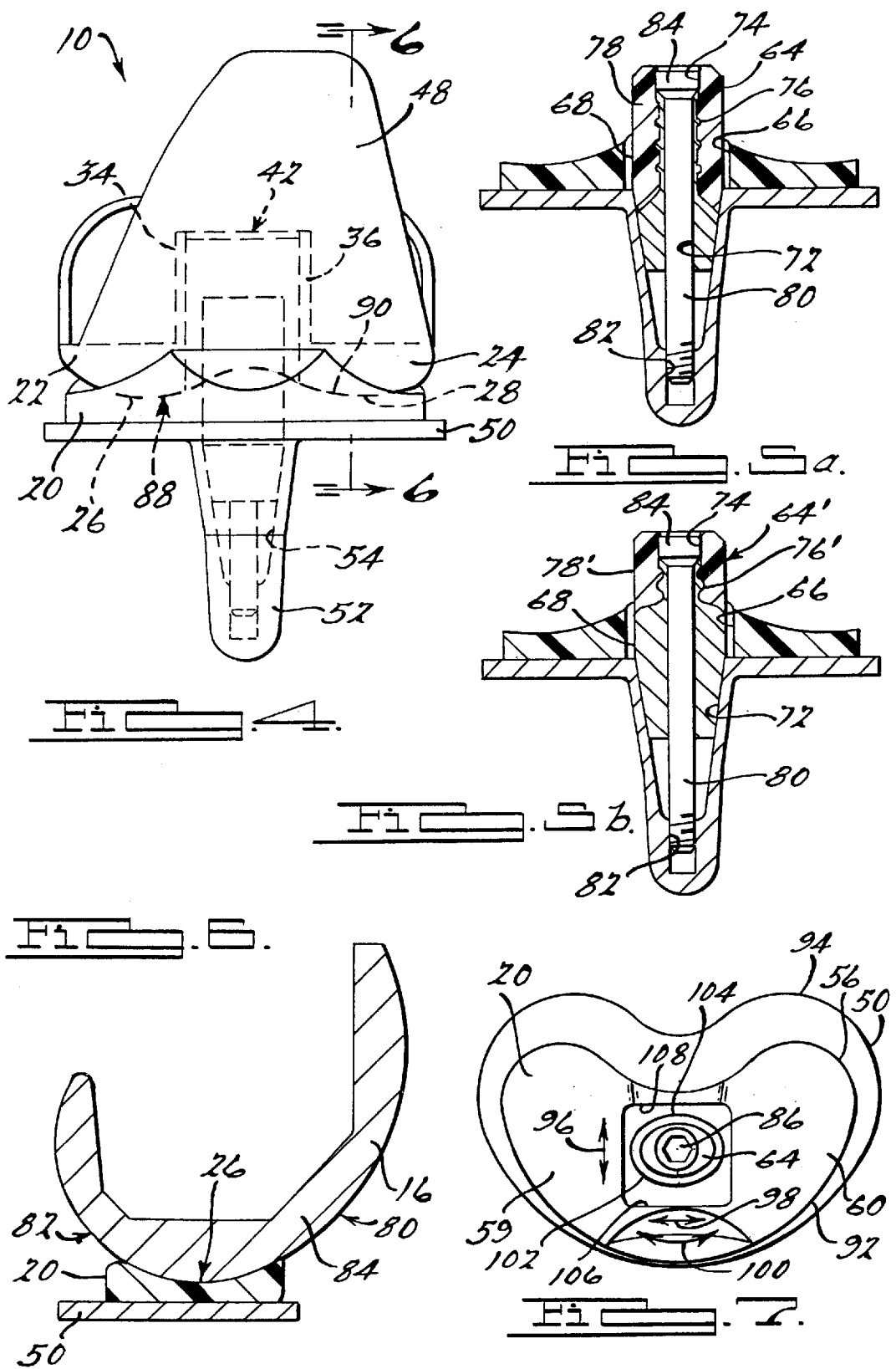

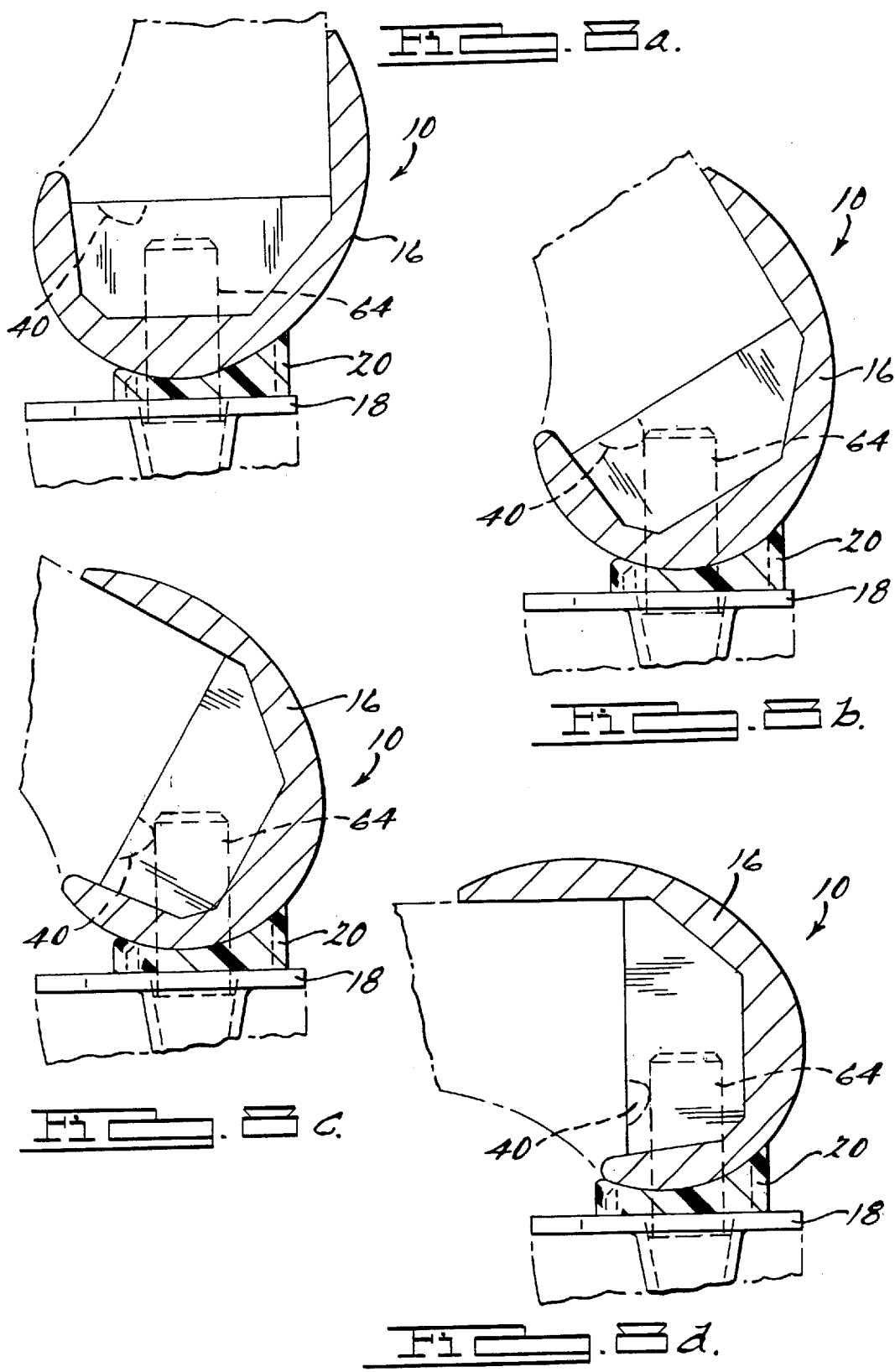

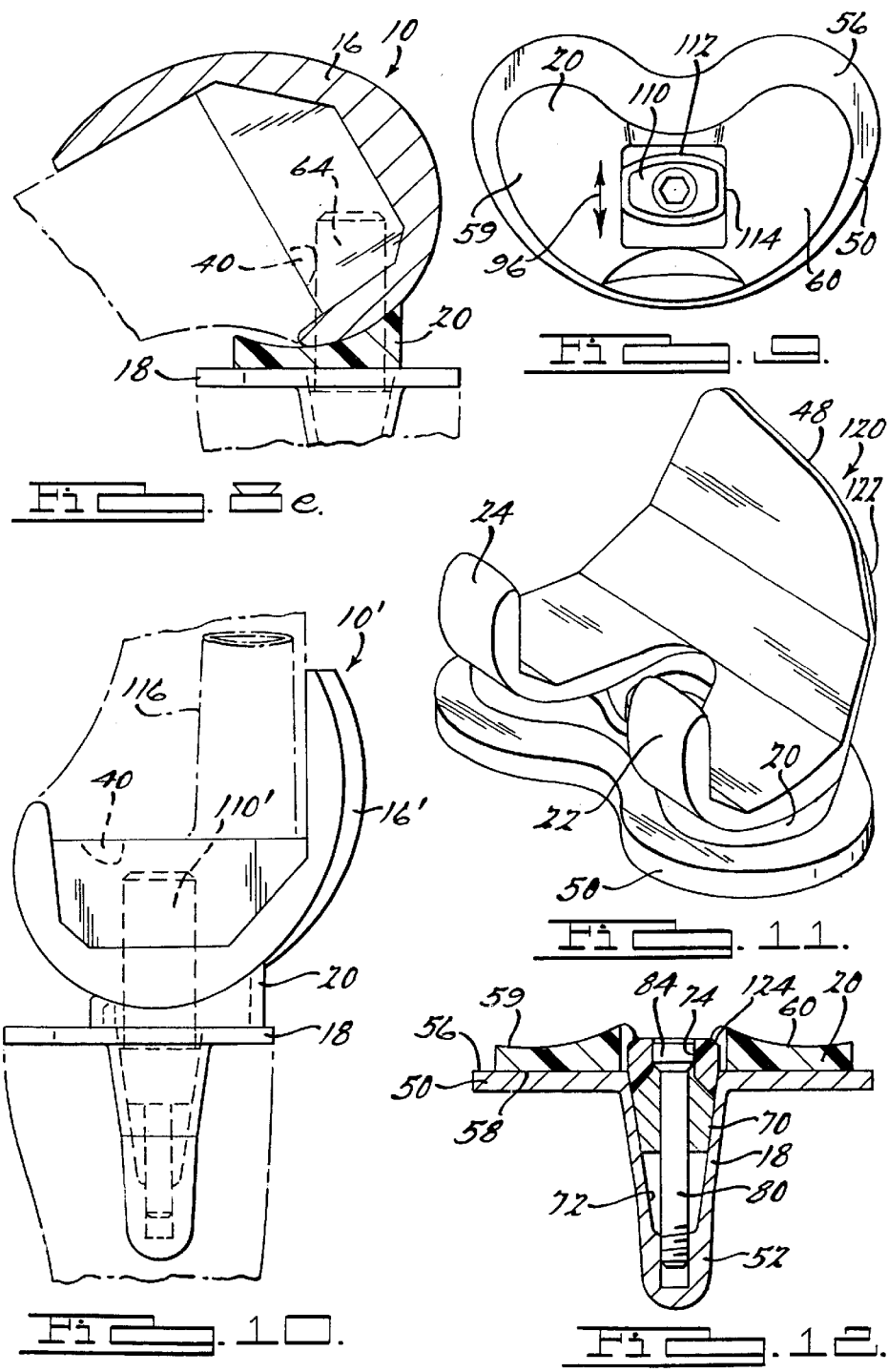

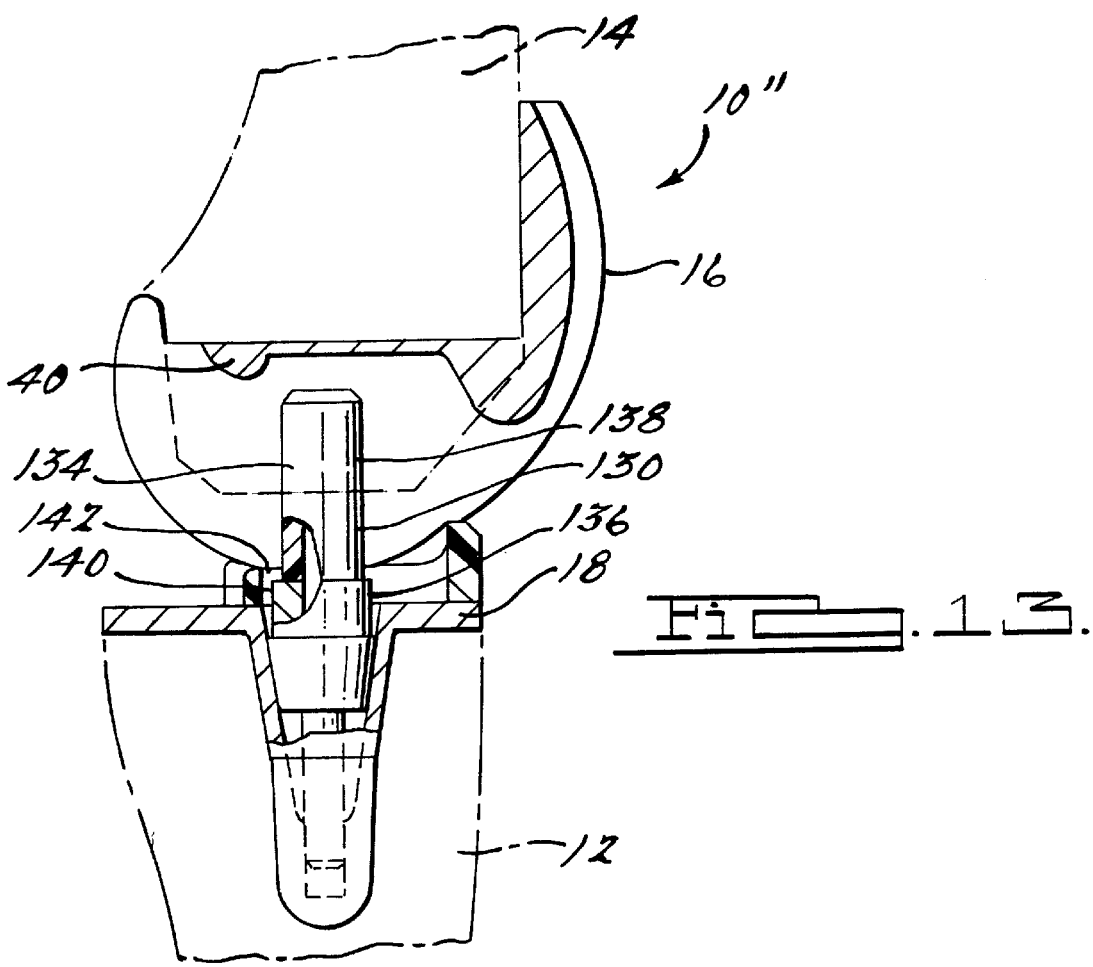

FLOATING BEARING KNEE JOINT PROSTHESIS WITH A FIXED TIBIAL POST

CROSS REFERENCE TO RELATED APPLICATION

This is a continuation-in-part application of U.S. Ser. No. 09/259,873, filed Mar. 1, 1999, now U.S. Pat. No. 6,165,223 entitled "Floating Bearing Knee Joint Prosthesis With a Fixed Tibial Post," which is now pending.

BACKGROUND OF THE INVENTION

1. Field of the Invention

This invention relates generally to a knee joint prosthesis which replaces the articulating knee portion of the femur and tibia, and more particularly, to a floating bearing knee joint prosthesis having a fixed tibial post.

2. Discussion of the Related Art

A knee joint prosthesis typically comprises a femoral component and a tibial component. The femoral component and the tibial component are designed to be surgically attached to the distal end of the femur and the proximal end of the tibia, respectively. The femoral component is further designed to cooperate with the tibial component in simulating and articulating motion of an anatomical knee joint.

Motion of a natural knee is kinematically complex. During a relatively broad range of flexion and extension, the articular or bearing surfaces of a natural knee experience rotation, medial and lateral angulation, translation in the sagittal plane, rollback and sliding. Knee joint prostheses, in combination with ligaments and muscles, attempt to duplicate this natural knee motion, as well as absorb and control forces generated during the range of flexion. Depending on the degree of damage or deterioration of the knee tendons and ligaments, however, it may be necessary for a knee joint prosthesis to eliminate one or more of these motions in order to provide adequate stability.

While knee joint prostheses are effective in replacing the anatomical knee joint, they nevertheless follow different design options that each have different advantages and disadvantages. For example, many knee joint prostheses are polycentric, such that the posterior femoral radius is smaller than the distal femoral radius. The reason for the change in radius is to provide an appropriately sized femoral component, facilitate early rollback, and to allow for full flexion. However, because of the smaller posterior femoral radius, such knee joint prostheses provide a large articulating contact area in extension, but as the knee joint prosthesis moves during flexion, the smaller posterior radius creates a smaller articulating contact area as flexion increases. This generally reduces the contact area from a large surface contact area to a smaller contact area between the femoral component and the tibial component. For example, the contact area may be about 275 mm$^2$ at extension and reduce substantially to about 75 mm$^2$ at 60° to 90° of flexion. This reduced contact area may not be optimal for long term durability due to increased contact stresses.

Other knee joint prostheses attempt to eliminate this disadvantage by using a roller and trough articulation, where the roller and trough are spherically or cylinderally shaped to provide full contact area throughout the range of motion from extension to flexion. However, the disadvantage with most of these type knee joint prostheses is that posterior rollback of the femoral component relative to the tibial component is eliminated. Such rollback is extremely desirable because it increases the extension moment arm, increases quadriceps efficiency, and helps patients perform activities of daily living, such as climbing stairs. In addition, these types of designs are typically rotationally constrained.

Other knee joint prostheses attempt to eliminate the above disadvantages using another design option, such as a meniscus or floating bearing between the femoral component and the tibial component. By utilizing a floating bearing, the articulating contact area between the femoral component and the bearing can theoretically be increased without increasing constraint. However, some of the knee joint prostheses that provide a floating bearing rely on ligaments for femoral rollback which in many cases may not be reliable. Moreover, some floating bearings may dislocate due to the shape of the bearing itself and the moment arms generated during rollback.

Knee joint prostheses are also generally provided having different levels of constraint. For example, primary type knee joint prostheses provide the least level of constraint, posterior stabilized (PS) knee joint prostheses provide an intermediate level of constraint, while fully constrained type knee joint prostheses provide the highest level of constraint upon the kinematic motions of a knee joint. In some situations, a patient may initially have a less constrained type knee joint implanted, such as a primary or posterior stabilized (PS) knee joint prosthesis. Should the patient later require a fully constrained type knee joint prosthesis because the patient is exhibiting instability, a surgeon is generally required to remove the entire knee joint prosthesis and implant both a new femoral and tibial component or a new fixed bearing to provide a fully constrained knee joint prosthesis. However, such extensive surgical modifications increases the overall surgical cost and complexity of upgrading a knee joint prosthesis from one constraint to another.

What is needed then is a knee joint prosthesis which does not suffer from the above mentioned disadvantages. This in turn, will provide a substantially conforming contact area between the articulating surfaces of the femoral component and the tibial component after extension, provide an increasing articulating contact surface area from extension through flexion, reduce overall stresses and wear in the articulating contact area, provide femoral rollback relative to the tibial component by means of a floating bearing, provide a floating bearing that reduces or eliminates bearing dislocation, provide a floating bearing which may reduce soft tissue impingement in extension, provide a mechanical engagement mechanism to force femoral rollback without having to rely on soft tissue ligaments, increase the overall reliability of the knee joint prosthesis, prevent anterior movement of the bearing and provide a modular knee joint prosthesis that can achieve different levels of constraint by simply replacing a guide post that is fixed to the tibial component. It is, therefore, an object of the present invention to provide a floating or rotating bearing knee joint prosthesis with a fixed tibial post that achieves the above-identified advantages.

SUMMARY OF THE INVENTION

In accordance with the teachings of the present invention, a floating or rotating bearing knee joint prosthesis with a fixed tibial post for use in replacing the articulating knee portion of a femur and a tibia is disclosed. The floating bearing knee joint prosthesis with the fixed tibial post provides a contact surface that increases between a femoral component, a tibial component and a bearing member as flexion increases.

In one preferred embodiment, a knee joint prosthesis for replacing an articulating portion of a femur and a tibia includes a femoral component, a tibial component, a guide post and a bearing member. The femoral component includes an engagement member, a first femoral bearing surface and a second femoral bearing surface. The tibial component includes a tibial bearing surface. The guide post extends from the tibial component and is operable to be engaged by the engagement member of the femoral component. The bearing member includes a first bearing surface that articulates with the first femoral bearing surface, a second bearing surface that articulates with the second femoral bearing surface and a third bearing surface that articulates with the tibial bearing surface. The bearing member also includes a posterior lip extension extending posteriorly from said third bearing surface, such that the bearing member is substantially inhibited from dislocating upon flexion of the knee joint prosthesis.

In another preferred embodiment, the knee joint prosthesis includes a femoral component, a tibial component, a guide post and a bearing member. The femoral component includes an engagement member, a first femoral bearing surface and a second femoral bearing surface. The tibial component includes a tibial bearing surface. The guide post extends from the tibial component and is operable to be engaged by the engagement member of the femoral component. The bearing member includes a first bearing surface that articulates with the first femoral bearing surface, a second bearing surface that articulates with the second femoral bearing surface and a third bearing surface that articulates with the tibial bearing surface. The bearing member also defines an opening passing through the bearing member which receives the guide post through the opening in the bearing member. The guide post and opening are configured to substantially inhibit rotational movement of the bearing member relative to the tibial component in extension while providing greater rotational freedom of the bearing member relative to the tibial component as flexion of the knee joint prosthesis increases.

In yet another preferred embodiment, the knee joint prosthesis includes a femoral component, a tibial component, a guide post and a bearing member. The femoral component includes an engagement member, a first femoral bearing surface and a second femoral bearing surface. The tibial component includes a tibial bearing surface. The guide post extends from the tibial component and is operable to be engaged by the engagement member of the femoral component. The guide post also includes a pair of anterior lobes extending from the guide post. The bearing member includes a first bearing surface that articulates with the first femoral bearing surface, a second bearing surface that articulates with the second femoral bearing surface and a third bearing surface that articulates with the tibial bearing surface. The bearing member also defines an opening passing through the bearing member, such that the pair of anterior lobes are operable to engage a sidewall that defines the opening to control rotational movement of the bearing member relative to the tibial component.

The use of the present invention provides a floating bearing knee joint prosthesis with a fixed tibial post. The floating bearing knee joint prosthesis provides a contact surface that increases between its components as flexion increases. As a result, the aforementioned disadvantages associated with the currently available knee joint prostheses have been substantially reduced or eliminated.

BRIEF DESCRIPTION OF THE DRAWINGS

Still other advantages of the present invention will become apparent to those skilled in the art after reading the following specification and by reference to the drawings in which:

FIG. 1 is a perspective view of a posterior stabilized (PS) knee joint prosthesis according to the teachings of a first preferred embodiment of the present invention;

FIG. 2 is an exploded perspective view of a tibial component and bearing element of the posterior stabilized (PS) knee joint prosthesis of FIG. 1;

FIG. 3 is a sagittal elevational view of the posterior stabilized (PS) knee joint prosthesis shown in FIG. 1 with a tibia and a femur of the natural knee shown in phantom;

FIG. 4 is a coronal elevational view of the posterior stabilized (PS) knee joint prosthesis shown in FIG. 1;

FIG. 5a is a coronal sectional view of the tibial component and bearing member of the posterior stabilized (PS) knee joint prosthesis of FIG. 3;

FIG. 5b is a coronal sectional view of the tibial component and bearing member of the posterior stabilized (PS) knee joint prosthesis of FIG. 3 according to the teaching of a second preferred embodiment of the present invention;

FIG. 6 is a sagittal sectional view of the posterior stabilized (PS) knee joint prosthesis taken through line 6—6 of FIG. 4;

FIG. 7 is a top view of the assembled tibial component and bearing member of FIG. 1;

FIGS. 8a–8e are partial sagittal sectional views of the posterior stabilized (PS) knee joint prosthesis shown in FIG. 1 illustrating five different positions of the femoral component with respect to the tibial component during a range of flexion from full extension to full flexion;

FIG. 9 is a top view of an assembled tibial component and bearing component of a fully constrained knee joint prosthesis according to the teachings of a second preferred embodiment of the present invention;

FIG. 10 is a sagittal elevational view of the fully constrained knee joint prosthesis of FIG. 9 with the tibia and the femur of the natural knee shown in phantom;

FIG. 11 is a perspective view of a primary knee joint prosthesis according to the teachings of a third preferred embodiment of the present invention;

FIG. 12 is a coronal sectional view of the tibial component and bearing member of the primary knee joint prosthesis of FIG. 11;

FIG. 13 is a partial sagittal sectional view of a posterior stabilized (PS) knee joint prosthesis according to the teachings of a fourth preferred embodiment of the present invention;

DETAILED DESCRIPTION OF THE PREFERRED EMBODIMENT(S)

Figures 14, 16:
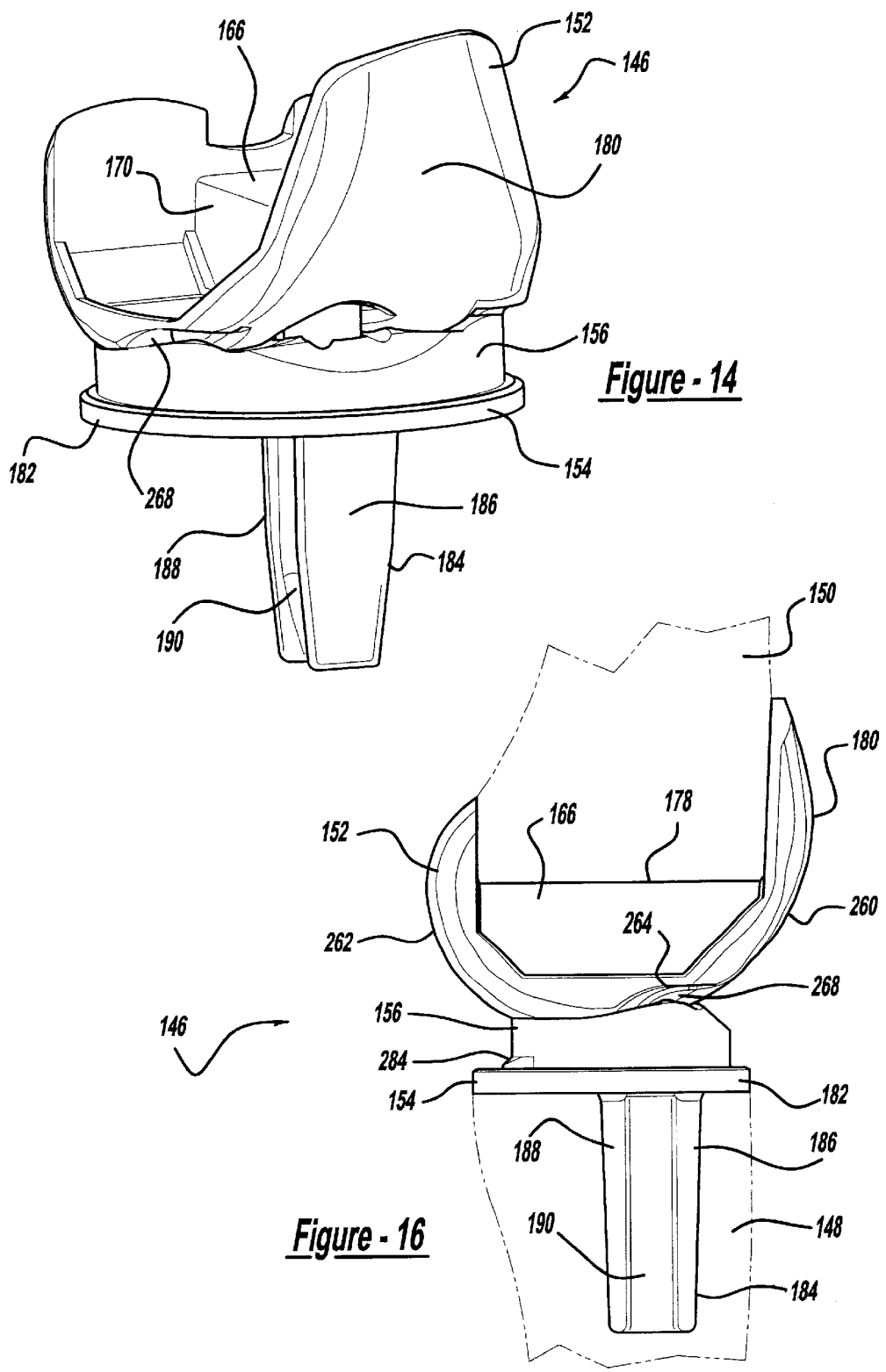
FIG. 14 is a perspective view of a posterior stabilized (PS) knee joint prosthesis according to the teachings of a fifth preferred embodiment of the present invention.
FIG. 16 is a sagittal elevational view of the posterior stabilized (PS) knee joint prosthesis, shown in FIG. 14 with a tibia and a femur of the natural knee shown in phantom.
Figure 15:
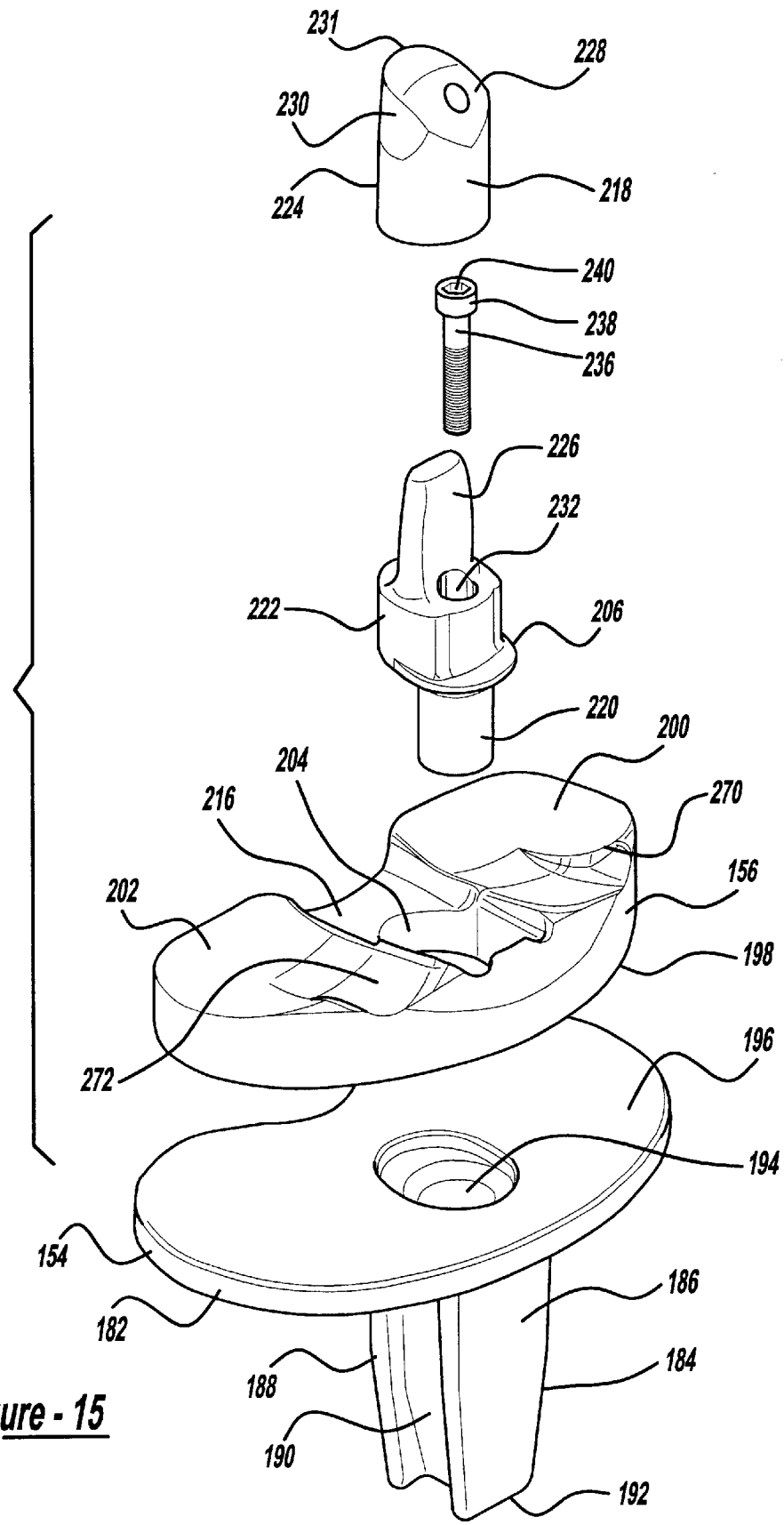
FIG. 15 is an exploded perspective view of a tibial component and bearing element of the posterior stabilized (PS) knee joint prosthesis of FIG. 14.
Figures 17, 18:
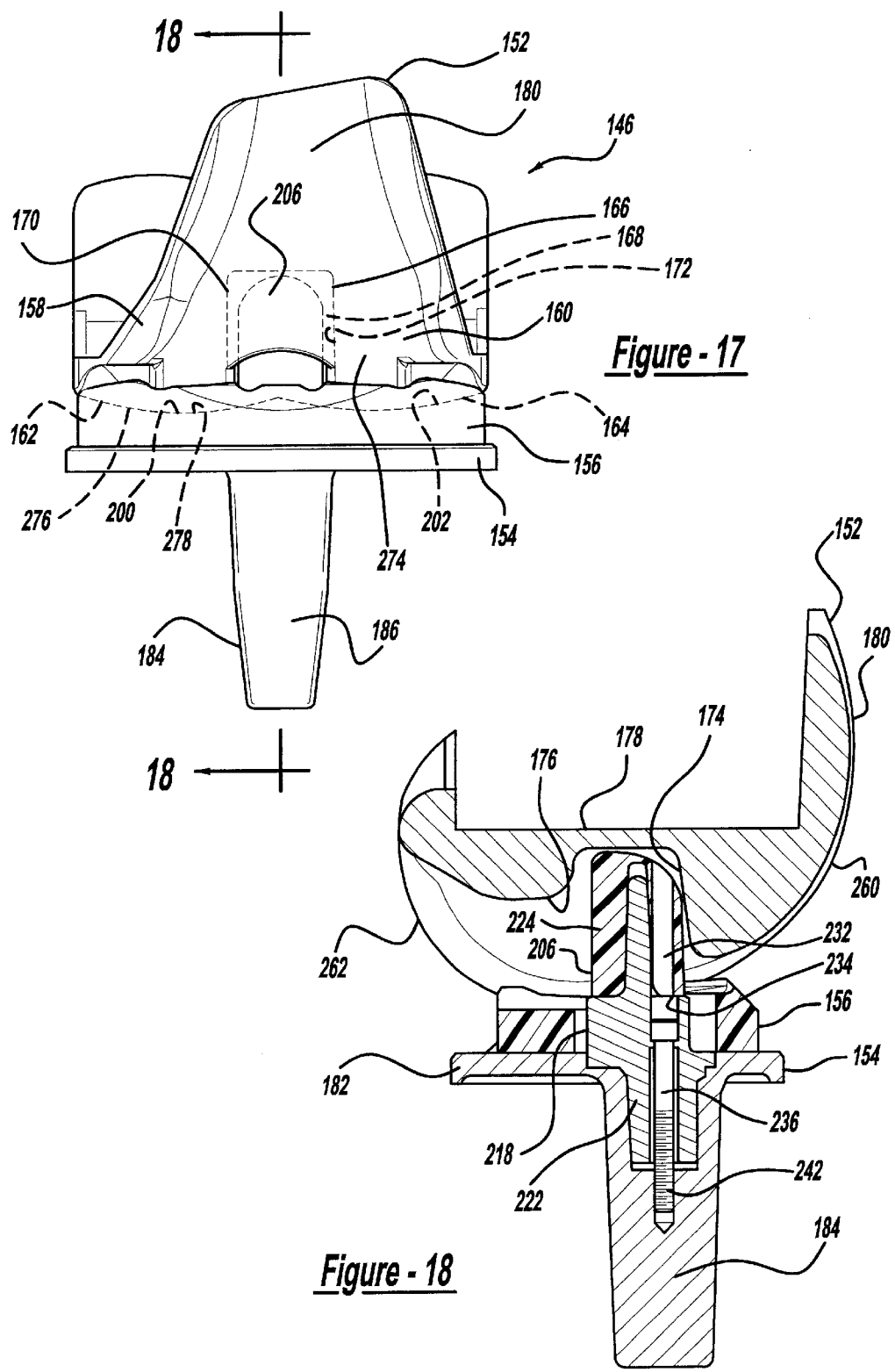
FIG. 17 is a coronal elevational view of the posterior stabilized (PS) knee joint prosthesis shown in FIG. 14.
FIG. 18 is a sagittal sectional view of the posterior stabilized (PS) knee joint prosthesis of FIG. 14 taken about line 18—18 of FIG. 17.
Figure 19:
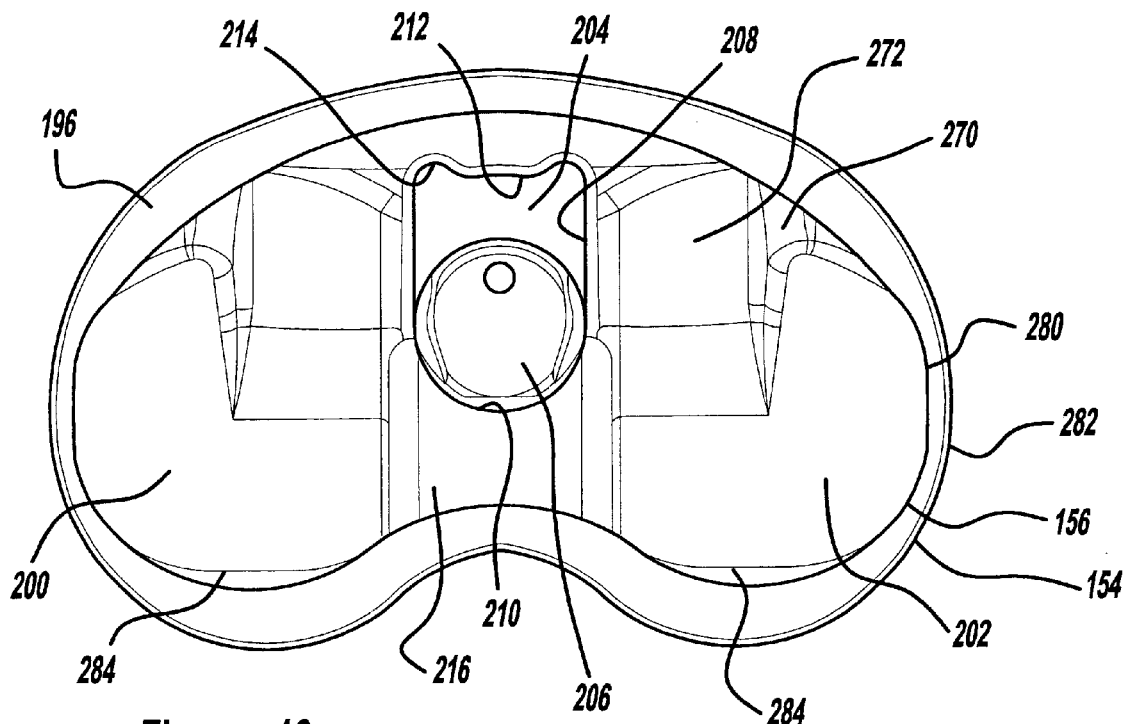
FIG. 19 is a top view of the assembled tibial component and bearing member of the posterior stabilized (PS) knee joint prosthesis of FIG. 14.

The following description of the preferred embodiments concerning a floating bearing knee joint prosthesis with a fixed modular tibial post are merely exemplary in nature and are not intended to limit the invention or its application or uses. Moreover, while the present invention is described in detail below generally with respect to a posterior stabilized (PS) knee joint prosthesis, it will be appreciated by those skilled in the art that the present invention is clearly not limited to only a posterior stabilized (PS) knee joint prosthesis and may be applied to various other types of knee joint prosthesis such as a primary knee joint prosthesis and a fully constrained knee joint prosthesis, as further discussed herein.

Referring to FIGS. 1–4, there is shown a knee joint prosthesis 10 according to the teachings of a first preferred embodiment of the present invention. The knee joint prosthesis 10 is generally known as a posterior stabilized (PS) knee joint prosthesis 10 which is designed to provide adequate stability in case of moderate deterioration or instability of the human knee. This most typically occurs when the anterior and posterior cruciate ligaments are sacrificed or dysfunctional and the medial and lateral collateral ligaments remain functionally intact. The knee joint prosthesis 10 is shown in FIGS. 3 and 4 as being secured to a tibia 12 and a femur 14 of a surgically resected left knee joint, with the tibia 12 and the femur 14 shown in phantom, and with the understanding that a suitable right knee joint prosthesis can be similarly constructed. The knee joint prosthesis 10 includes a femoral component 16, a tibial component 18 and a floating tibial bearing 20.

The femoral component 16 is adapted to be secured to a distal end of the femur 14 and includes a first condylar portion 22 and a second condylar portion 24 that provide a first femoral bearing surface 26 and a second femoral bearing surface 28, respectively. The first and second condylar portions 22 and 24 of the femoral component 16 are interconnected by an intercondylar portion 30 that defines an intercondylar recess 32. The intercondylar portion 30 includes a first lateral sidewall 34 and a second lateral sidewall 36 that are substantially planar and parallel to one another. The anterior portions of the first and second lateral sidewalls 34 and 36 are connected by an anterior wall 38 and the posterior portions of the first and second lateral sidewalls 34 and 36 are connected by a posterior engagement member or elongated cam 40. The intercondylar portion 30 which includes the first and second lateral sidewalls 34 and 36, the anterior wall 38 and the posterior engagement member 40 define the perimeter of a box 42 that defines the intercondylar recess 32.

Positioned atop the box 42 is a substantially planar integral top 44 that defines an elongated opening or bore 46. A closed box may also be utilized in place of the open box 42. The femoral component 16 further includes an arcuate patellar portion 48 which is disposed on the anterior surface of the femoral component 16. The patellar portion 48 is shaped to allow anatomical tracking of a natural or prosthetic patella. The patella prostheses which are compatible with the present invention may be of varying shape, such as round or dome shaped and may be constructed from polyethylene, polyethylene with metal backing or other suitable materials. The femoral component 16 including the box 42 is preferably formed as a unitary structure and preferably cast of a biocompatible high strength alloy, such as a cobalt-chromium-molybdenum alloy or other suitable material. All surfaces which do not contact the femur 14 are preferably highly polished to provide smooth articulating bearing surfaces.

The tibial component 18 is adapted to be secured to the proximal end of the tibial 12 after the tibia has been resected in a manner known in the art. The tibial component 18 includes a substantially planar platform-like tibial tray 50 and an inferiorly extending tibial stem 52. The tibial stem 52 is adapted to be received in a corresponding opening made by the surgeon in the longitudinal center of the tibia 12. The tibial tray 50 and the tibial stem 52 define a conically shaped bore 54 axially extending through the tibial tray 50 and into the stem 52. The tibial tray or plateau 50 and stem 52 are preferably manufactured from cobalt-chromium-molybdenum or any other suitable biocompatible material. The top of the tibial tray 50 is highly polished to provide a substantially smooth tibial bearing surface 56.

The floating or rotating bearing 20 is located between the femoral component 16 and the tibial component 18. The floating bearing 20 has a substantially planar inferior bearing surface 58 which slidably moves relative to the highly polished tibial bearing surface 56, further discussed herein. The floating bearing 20 further includes a first superior articulating or bearing surface 59 and a second superior articulating or bearing surface 60. The first bearing surface 59 and the second bearing surface 60 articulate with the first bearing surface 26 of the condyle 22 and the second bearing surface 28 of the condyle 24 of the femoral component 16. Positioned between the first and second bearing surfaces 59 and 60 is a substantially rectangular opening 62 that is slidably positioned about a center modular guide post 64. The opening 62 is defined by a substantially perpendicular peripheral sidewall 66 which is operable to engage the center guide post 64. The floating bearing 20 is preferably formed from a surgical grade, low friction, low wearing plastic, such as UHMWPE or other suitable material.

The center guide post 64 includes a substantially oval shaped outer peripheral sidewall 68 or any other appropriately shaped sidewall and a conically tapered sidewall 70. The conically tapered sidewall 70 is operable to be nestingly received within the conically tapered bore 54 to provide a friction fit that forms a Morse-type taper. Alternatively, the center guide post 64 may be formed integral with the tibial component 18. Extending axially through the center guide post 64 is a substantially cylindrical bore 72 having a superiorly located counterbore 74, as shown clearly in FIG. 5a. The center guide post 64 is formed from a combination of a cobalt-chromium-molybdenum portion 76 and a molded polymer portion 78 formed from UHMWPE or other suitable material. The polymer portion 78 extends to the base of the tibial tray 50 to provide a polymer/polymer contact between the centering post 64 and the floating bearing 20, via sidewalls 66 and 68.

Axially extending through the bore 72 is a threaded bolt 80 which threadably engages a threaded bore 82 located inferiorly of the stem 52. The bolt 80 further includes a head 84 which is nestingly received within counterbore 74. The head 84 includes a hexagonal drive 86 that may be rotatably engaged by a hexagonal drive member. Upon threadably engaging bolt 80 within bore 82, the centering post 64 is rigidly secured, via the Morse-type taper formed from the conical bore 54 and the conical sidewall 70.

Referring to FIG. 5b, a second embodiment of a centering post 64' is shown. In this regard, like reference numerals will be used to identify like structures with respect to the centering post 64. The centering post 64' is substantially similar to the centering post 64 except that the metal portion 76' extends above the tibial tray 50, thereby providing a reduced or smaller polymer portion 78'. In this configuration, a polymer/metal contact or interface is formed between the floating bearing 20 and the centering post 64', via the sidewalls 66 and 68.

Turning to FIGS. 4 and 6, the articulating bearing surfaces 26 and 28 of the first and second condyles 22 and 24 of the femoral component 16 are shown cooperating with the bearing surfaces 59 and 60 of the floating bearing 20. In this regard, each condyle 22 and 24 of the femoral component 16 has a polycentric bearing surface 26 and 28, respectively along the sagittal plane. In other words, each bearing surface 26 and 28 is defined by a large anterior radius 80 and a smaller posterior/distal radius 82. The large anterior radius 80 is preferably about 1.497 inches and extends to about point 84. The posterior/distal radius 82 is about 0.945 inches and extends anterior the center line of the femoral component 16 up to point 84. Point 84 is located just anterior the floating bearing 20. Correspondingly, the bearing surface 59 and 60 of the floating bearing 20 are formed with a single radius 86 along the sagittal plane having a radius of about 0.945 inches. Because the sagittal posterior/distal radius 82 of the femoral component 16 extends beyond the axial center line of the femoral component 16 anteriorly to point 84, this radius congruently mates with the radius 86 of the floating bearing 20 from extension to full flexion. This mating provides a substantially fully mated and constant contact surface area between the femoral component 16 and the floating bearing 20 substantially through extension and flexion along the sagittal plane.

Each bearing surface 26 and 28 of the condyles 22 and 24 are arcuately shaped with a constant radius 88 of about 1.6 inches along the coronal plane. Correspondently, the bearing surfaces 59 and 60 of the floating bearing 20 are likewise, formed from a constant radius 90 of about 1.6 inches along the coronal plane. Each of the radii 88 and 90 congruently mate with one another to provide substantially full surface contact along the coronal plane from extension to flexion. This full surface contact along both the sagittal and coronal planes substantially evenly disburses stresses between the femoral component 16 and the floating bearing 20, as opposed to femoral components, which merely provide a smaller contact area, such as a line or point contact, either along the sagittal plane or the coronal plane which focuses stresses at these contact points, thereby potentially increasing wear in these areas. In other words, a contact area of greater than about 300 mm$^2$ is maintained from extension to full flexion between the femoral component 16 and the floating bearing 20.

Referring now to FIG. 7, a top view of the assembled tibial component 18, along with the floating bearing 20 is shown. In this regard, the floating bearing 20 has an outer peripheral wall 92 which is substantially concentric with the outer peripheral wall 94 of the tibial tray 50. With the floating bearing 20 positioned atop the tibial tray 50 in extension, the guide post 64 is positioned just posteriorly the opening 62 defined by sidewall 66. It should be noted that the post 64 is sized relative to the opening 62 such that the posterior stabilized knee joint prosthesis 10 provides anterior and posterior movement 96, medial to lateral movement 98, and rotation movement 100 of the floating bearing 20 relative to the tibial component 18. Moreover, the femoral component 16 provides rotational movement along the sagittal plane relative to the floating bearing 20, as well as varus and valgus movement relative to the floating bearing 20. The posterior stabilized knee joint prosthesis 10 may also simply provide the anterior to posterior movement 96 and the rotational movement 100 and eliminate the medial to lateral movement 98 of the floating bearing 20 relative to the tibial tray 50.

Turning to FIGS. 8a–8e, partial sagittal sectional views of the posterior stabilized (PS) knee joint prosthesis 10 illustrating the movement of the femoral component 16 and the floating bearing 20 relative to the tibial component 18 are shown from full extension in FIG. 8a to full flexion in FIG. 8e. In FIG. 8a, the posterior stabilized (PS) knee joint prosthesis 10, both anteriorly and posteriorly, is inherently stable at full extension when the patient is standing. In this position, the first and second femoral bearing surfaces 26 and 28 are rested within the first and second tibial bearing surfaces 59 and 60 of the floating bearing 20, respectively. The anterior surface 102 and the posterior surface 104 of the post 64 do not engage the anterior portion 106 or the posterior portion 108 of the sidewall 66. The posterior surface 104 of the post 64 further does not engage the engagement member 40 of the femoral component 16. If the knee joint prosthesis 10 would undergo a large hyper-extension or forward rollback (approximately 10°), the anterior surface 102 of the post 64 would engage the anterior portion 38 of box 42 in the femoral component 16, while the floating bearing 20 would generally slide posteriorly relative to the tibial tray 50. This engagement will further avoid posterior dislocation of the femoral component 16 relative to the tibial component 18.

The femoral component 16 with respect to the tibial component 18 and the floating bearing 20 is generally most unrestricted between full extension, as illustrated in FIG. 8a and the point of flexion where the posterior engagement member 40 and the posterior surface 104 of the post 64 initially engage, as illustrated in FIG. 8b. This engagement generally occurs between about 20° to 45° of flexion. Within this range between 0° to about 20° to 45°, the femoral component 16 is permitted to translate in the sagittal plane along with the floating bearing 20 relative to the tibial component 18. In particular, the femoral component 16 will remain substantially congruently positioned relative to the floating bearing 20 to provide a full articulating contact surface during this range of flexion. In other words, the femoral component 16 and the floating bearing 20 are both able to move anteriorly and posteriorly relatively freely with respect to the tibial component 18, via the bearing surfaces 56 and 58 between the floating bearing 20 and the tibial tray 50. However, it should be further understood that the exact amount of translation in the sagittal plane permitted by the knee joint prosthesis 10 will of course, vary depending on the forces imparted by local soft tissues, muscles, tendons, ligaments, as well as forces transmitted from the tibia and fibula. These forces will, of course, vary from patient to patient, from activity to activity, as well as from implantation to implantation.

When flexion exceeds approximately 20° to 45°, as shown in FIG. 8c, the posterior engagement member 40 of the femoral component 16 engages the posterior surface 104 of the post 64. This engagement forces rollback of the floating bearing 20 posteriorly relative to the tibial tray 50, whereby the floating bearing 20 having bearing surface 58 slides relative to bearing surface 56 of tibial tray 50. While this forced rollback of the floating bearing 20 is occurring, the bearing surfaces 26 and 28 of the first and second condyles 24 and 26 are fully nestingly received within the bearing surfaces 59 and 60 of the floating bearing 20. This forced rollback of the floating bearing 20 creates the desired femoral rollback of an anatomical knee joint. As flexion continues from about 60° shown in FIG. 8c to about 110° shown in FIG. 8e, a forced rollback of the floating bearing 20 relative to the tibial tray 50 continues to occur, while a full surface contact area between the first and second condyles 22 and 24 and the floating bearing 20 are maintained, via cooperating surfaces 26, 28 and 59, 60, respectively.

As can be observed from FIGS. 8a–8e, the forced rollback provided by the engagement of the fixed modular post 64 with the engagement member 40 enables a full surface contact area to be maintained between the femoral component 16 and the floating bearing 20. This full surface contact is achieved because rollback is occurring between the floating bearing 20 and the tibial component 18, via a sliding of the floating bearing 20 posteriorly atop the tibial tray 50 with surfaces 56 and 58. This is in contrast to existing fixed bearing knee prostheses which achieve rollback, via the translation of the femoral component relative to a fixed bearing atop the tibial component. With conventional floating bearing knee prostheses, these devices either do not provide any type of guide post secured to the tibia and simply rely on soft tissue to produce the rollback or they utilize a post which is integral with the floating bearing. Accordingly, the rollback in the prior art is again occurring between the femoral component 16 and the floating bearing 20, as opposed to the floating bearing 20 and the tibial component 18, which provides a substantially increased surface area during rollback for overall reduced wear of the bearing member 20.

Turning to FIG. 9, a top view of the tibial component 18 and the floating bearing 20 is shown with a fully constrained guide post 110. In this regard, the post 110 is substantially similar to the post 64, except that the outer peripheral wall 112 is oval with truncated ends 114. In this regard, the endwalls 114 slidably engage the sidewalls 66 of opening 62, thereby eliminating any lateral or medial movement 98 or rotational movement 100 with respect to the tibial component 18. This fully constrained type knee therefore, only allows anterior and posterior movement 96 of the floating bearing 20 relative to the tibial component 18. Thus, by simply replacing the post 64 with a new post 110, the knee joint prosthesis 10 may be converted from a posterior stabilized (PS) knee joint prosthesis 10 to a fully constrained knee joint prosthesis 10'. This provides for a fully constrained knee that maintains the large contact area (i.e. >300 mm$^2$), as well as having the desired rollback. It should further be noted that by simply changing the shape of the post 64, cam member 40, or the opening 62 in the bearing 20, the anterior motion may be adjusted. Moreover, removable sleeves may be fashioned that slide on to post 64 to provide for further adjustment.

This convertibility enables a substantially convenient method for changing from a posterior stabilized (PS) to a fully constrained knee joint by simply replacing the guide post 64, via the threaded bolt 80. Should further stability be required with the femoral component 16, a closed box femoral component 16' may be used which includes a femoral stem 116. In this situation, the original femoral component 16 would be replaced with the new femoral component 16', while the tibial component 18 and the bearing component 20 would stay the same. It should further be noted that the movement of the femoral component 16, the tibial component 18 and bearing member 20 relative to one another along the sagittal plane is substantially similar to that shown in FIGS. 8a–8e of the posterior stabilized (PS) knee joint prosthesis 10.

Turning to FIGS. 11 and 12, a primary knee joint prosthesis 120 according to the teachings of a third preferred embodiment of the present invention is shown. In this regard, the tibial component 18 and the floating bearing 20 are substantially the same as used with the other preferred embodiments. The only differences are with respect to the femoral component 122 and the central post 124. In this regard, the post 124 is substantially similar to the post 64 except that the height of the post is reduced so that it does not extend above or out beyond the opening 62. The femoral component 122 includes the first and second condyles 22 and 24 having the first and second bearing surfaces 26 and 28, respectively. The femoral component 122 further includes the articulating patella portion 48. What is essentially missing is the box 42 which provides the posterior engagement member 40. Because of this, there is no mechanical engagement of the post 124 relative to the femoral component 122 to force a rollback of the floating bearing 20 relative to the tibial component 18.

The rollback of the floating bearing 20 is achieved by the remaining soft tissues and ligaments of the patient. In this regard, the floating bearing 20 is initially centrally positioned about the tibial tray 50 similar to the other preferred embodiments during full extension. At about 25° to 45° of flexion, rollback of the floating bearing 20 starts and is substantially maintained through full flexion because of the cruciate ligament causing the floating bearing 20 to roll back. Here again, the primary knee joint prosthesis 120 may be converted from a primary knee joint prosthesis 120 to a posterior stabilized (PS) knee joint prosthesis 10 or a fully constrained knee joint prosthesis 10' by simply replacing the post 124 and the femoral component 122 without having to change the tibial component 18 or the tibial bearing 20.

Turning to FIG. 13, a partial sagittal sectional view of a posterior stabilized (PS) knee joint prosthesis 10" according to the teachings of a fourth preferred embodiment of the present invention is shown. In this regard, like reference numerals will be used to identify like structures with respect to the knee joint prosthesis 10. In this regard, the only differences are with respect to the shape of the guide post 130 and the floating bearing 132. The guide post 130 is secured to the tibial component 18 in substantially the same manner as that shown with regard to the knee joint prosthesis 10. The difference in the guide post 130 is that it includes a first guide portion 134 and a second guide portion 136. The first guide portion 134 is defined by a substantially oval shaped sidewall 138 similar to that shown in FIG. 2. The second guide portion 136 is also formed by an oval sidewall 140 which is larger than the oval sidewall 138. The first guide portion 134 is preferably formed from a molded polymer, such as UHMWPE and the second guide portion 136 is preferably formed from a cobalt-chromium-molybdenum. However, various other combinations between the first guide portion 134 and the second guide portion 136 can also be provided such as a complete polymer assembly, complete metallic assembly or any other combination.

The second guide portion 136 has a height which does not extend beyond the bearing 134 and is positioned within opening 142 such that the second guide portion 136 only engages and controls the movement of the floating bearing 132 relative to the tibial component 18. The second guide portion 134 extends into the box 42 of the femoral component 16 such that the second guide portion 134 is operable to be engaged by the cam member 40 to control the movement of the femoral component 16 relative to the bearing 132. In other words, the two stage guide post 138 individually controls the relative movement of the femoral component 16 and the bearing component 132 with the first guide portion 134 and the second guide portion 136, respectively. This provides for increased adjustability in the relative articulating motion of the knee joint prosthesis 10" while further maintaining a substantially full and continuous contact area between the femoral component 16 and the floating bearing 132 from extension to full flexion.

Referring to FIGS. 14–20, there is shown a posterior stabilized (PS) knee joint prosthesis 146 according to the teachings of a fifth preferred embodiment of the present invention which is designed to provide adequate stability in case of moderate deterioration or instability of the human knee. The knee joint prosthesis 146 is shown in FIG. 16 as being secured to a tibia 148 and a femur 150 of a surgically resected left knee joint, with the tibia 148 and the femur 150 shown in phantom, and with the understanding that a suitable right knee joint prosthesis can be similarly constructed. Here again, the knee joint prosthesis 146 includes a femoral component 152, a tibial component 154 and a floating tibial bearing 156.

The femoral component 152 is adapted to be secured to the distal end of the femur 150 similar to the femoral component 16, shown in FIG. 1. The femoral component 152 includes a first condylar portion 158 and a second condylar portion 160 that provides a first femoral bearing surface 162 and a second femoral bearing surface 164, respectively (see FIG. 17). Here again, the first and second condylar portions 158 and 160 are inter-connected by an inner condylar portion 166 that defines an inner condylar recess 168. The inner condylar portion 166 is defined by first and second lateral sidewalls 170 and 172, anterior wall 174, posterior engagement member or cam 176 and top 178. The top 178 may either be an open or closed top, depending upon the desired configuration.

The femoral component 152 also includes an arcuate patellar portion 180 which is disposed on the anterior surface of the femoral component 152. The patellar portion 180 is shaped to allow anatomical tracking of a natural or prosthetic patella. Again, the patella prosthesis, which are compatible with the present invention may be of varying shapes, such as round or dome shaped and may be constructed from polyethylene, polyethylene with metal backing or other suitable materials. Additionally, the femoral component 152 is preferably formed as a unitary structure and cast from a biocompatible high strength alloy, such as cobalt-chromium-molybdenum alloy or other suitable biocompatible material. The surfaces which do not contact the femur 150 are preferably highly polished to provide smooth articulating bearing surfaces.

The tibial component 154 is substantially similar to the tibial component 18 and is likewise adapted to be secured to the proximal end of the tibial 148 after the tibia 148 has been resected in a manner known in the art. The tibial component 154 includes a substantially planar platform-like tibial tray 182 and an inferiorly extending tibial stem 184. The tibial stem 184 is adapted to be received in a corresponding opening made by a surgeon in the longitudinal center of the tibia 148. The tibial stem 184 is formed from a first planar member 186, which is positioned substantially perpendicular to the tibial plateau 182 and a second planar member 188 which is positioned at a slight angle relative to the perpendicular axis of member 186. Connecting member 186 with member 188 is a tapered member 190, which tapers at its distal end 192 to form a substantially I-beam cross-section. The tibial tray 182 and the tibial stem 184 define a conically shaped bore 194. Here again, the tibial tray 182 and the tibial stem 184 are preferably manufactured from cobalt-chromium-molybdenum, or any other suitable material with the top of the tibial tray 182 being highly polished to provide a substantially smooth tibial bearing surface 196.

The floating bearing 156 is positioned between the femoral component 152 and the tibial component 154. The floating bearing 156 includes a substantially planar inferior bearing surface 198 which slidably moves relative to the highly polished tibial bearing surface 196. The floating bearing 156 also includes a first superior articulating or bearing surface 200 and a second superior articulating or bearing surface 202. Positioned between the first and second bearing surfaces 200 and 202 is an elongated opening 204 that is slidably positioned about a guide post 206. The opening 204 is defined by a pair of opposed lateral sidewalls 208, a semi-circular or arcuate posterior sidewall 210 and an anterior sidewall 212 which has a pair of recessed lobes or ears 214. Extending posteriorly from the opening 204 is a recessed area 216 positioned or located between the first bearing surface 200 and the second bearing surface 202. The floating bearing 156 is also preferably formed from a surgical grade, low friction, low wearing plastic, such as UHMWPE or other suitable material.

The center guide post 206 includes a substantially cylindrically shaped outer peripheral sidewall 218 and a conically tapered sidewall 220. The conically tapered sidewall 220 is operable to be nestingly received within the conically tapered bore 194 to provide a friction fit formed by a Morse-type taper. It should further be noted that guide post 206 may also be formed integral with the tibial component 154. The guide post 206 is constructed from a combination of a cobalt-chromium-molybdenum portion 222 and a molded polymer portion 224 formed from UHMWPE or other suitable material. The non-polymer portion 222 extends up to the floating bearing 156 so that the floating bearing 156 contacts the cobalt-chromium-molybdenum cylindrical sidewall 218. The polymer portion 224 is molded to a post 226 and extends from above the floating bearing 156 into the recess 168, also having the outer cylindrical sidewall 218. The superior surface of the guide post 206 has an anterior arcuate surface 228 and planar tapered superior sidewalls 230. The anterior arcuate sidewall 228 reduces or eliminates impingement of the post 206 within the inner condylar portion 166 during hyper-extension of the knee joint prosthesis 146. The cylindrical sidewall 218 also includes a posterior planar sidewall portion 231, further discussed herein.

Extending through the center guide post 206 is a substantially cylindrical axial bore 232 having a stepped shoulder 234. The stepped shoulder 234 forms a retention mechanism to retain a threaded bolt 236 within the axial bore 232. In this regard, the non-polymer portion 222 of the guide post 206 is machined and tooled in the configuration shown. The threaded bolt 236 which includes a head 238 having a hexagonal drive 240 is then inserted into the bore 232. Thereafter, the polymer portion 224 is molded over the elongated post 226 with the subsequent bore 232 being formed therein to create the shoulder 234. The shoulder 234 captures or retains the bolt 236 within the non-polymer portion 222 of the center guide post 206. In this way, should the bolt 236 ever become loosened from threaded bore 242, it will not be free to enter the articulating area of the knee joint prosthesis 146. Thus, to rigidly secure the center guide post 206, the tapered sidewall 220 is matingly received within the tapered bore 194 and the bolt 236 is threadably engaged within bore 242 to securely hold the centering guide post 206 relative to the tibial component 154.

Figure 21:
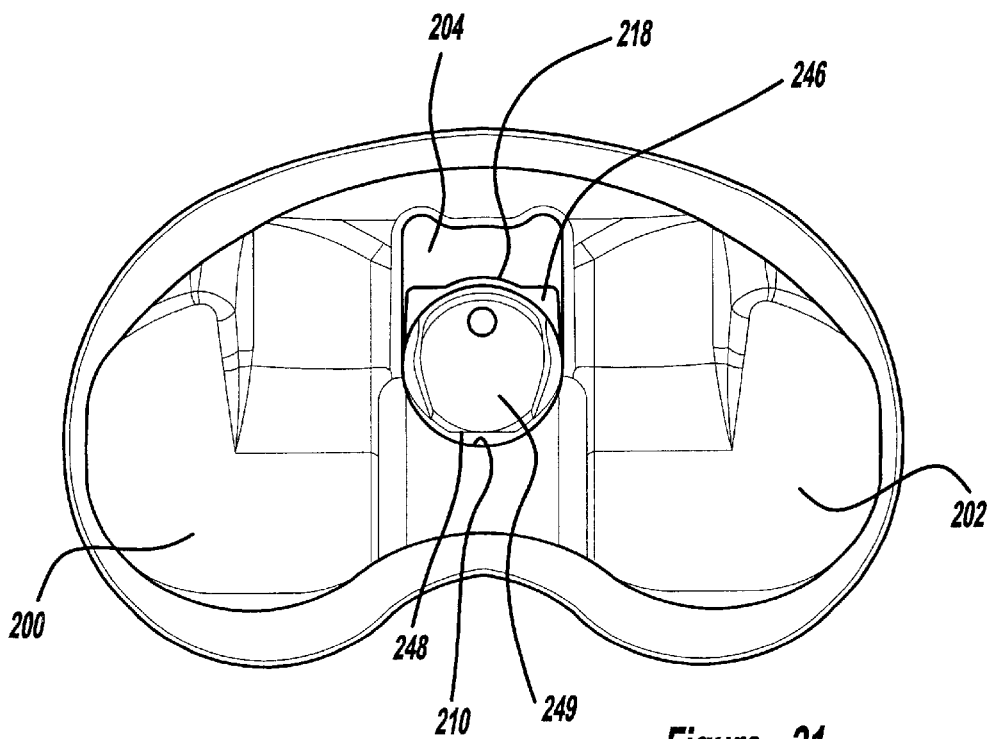
FIG. 21 is a top view of an assembled tibial component and bearing member according to the teachings of a sixth preferred embodiment of the present invention.

Referring to FIG. 21, another embodiment of a centering post 244 is shown. In this regard, like reference numerals will be used to identify like structures with respect to the centering post 206. The centering post 244 is substantially similar to the centering post 206, except that the non-polymer portion 222 of the cylindrical sidewall 218 includes a pair of arcuate lobes or ears 246 which extend anteriorly from the post 244. The arcuate lobes 246 extend anteriorly in the region of the floating bearing 146 and do not extend up beyond this region into the recess 168 of the femoral component 152, thereby providing two guide portions or regions in the guide post 244. It should also be noted that the arcuate lobes 246 may also extend posteriorly and achieve substantially the same level of rotational constraint as the anterior extending lobes 246. The guide post 244 also includes a posterior planar sidewall 248 extending throughout the length of the sidewall 218. This planar sidewall region 248 inhibits contact of the post 244 relative to the posterior sidewall 210 of the opening 204 formed within the bearing 156. In this regard, by preventing contact at the posterior most portion of the opening 204 where the thickness of the bearing wall is the thinnest, this disburses the force imparted by the post 244 to the thickest regions of the bearing 156, thereby enhancing distribution of the engagement force between the post 244 and the bearing 156.

The guide post 244 enables the bearing 156 to move anterior-posterior (A-P), as well as enables rotational movement of the bearing 156 relative to the tibial component 154, similar to the guide post 206. However, by providing the additional arcuate lobes 246, rotational movement is substantially limited to about +/−15°. In this regard, upon rotating the bearing 156 relative to the fixed post 244, the lateral sidewall 208 of the opening 204 will engage one of the arcuate lobes 246 upon rotation of about 15°, thereby preventing further rotation of the bearing member 156 relative to the guide post 244. This provides a more constrained knee joint prosthesis 146 as compared to the guide post 206. Therefore, by simply switching the guide post 206 with the guide post 244, the rotational translation of the knee joint prosthesis 146 can be changed or constrained to about +/−15°, while still providing the same A-P translation.

Figure 22:
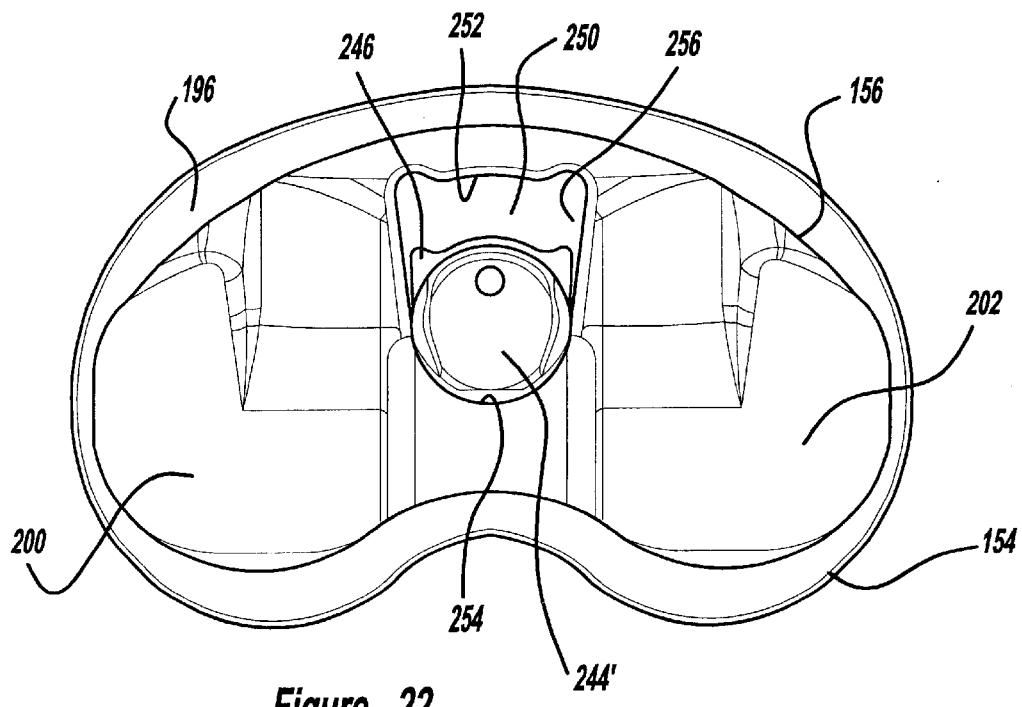
FIG. 22 is a top view of an assembled tibial component and bearing member according to the teachings of a seventh preferred embodiment of the present invention.

Referring now to FIG. 22, a guide post 244' is shown in use with the bearing 156 having a different shaped opening 250. In this regard, the opening 250 includes an anterior sidewall 252, a posterior sidewall 254 and a pair of angled lateral sidewalls 256. The angled lateral sidewalls 256 narrow the opening 250 posteriorly and widen the opening 250 anteriorly. With this configuration, when the knee joint prosthesis 146 is in extension, the guide post 244' somewhat engages the posterior sidewall 254 with the arcuate lobes 246 substantially aligning with the angled lateral sidewalls 256, such that there is little or no rotation of the bearing 156 relative to the post 244' in extension. As there is flexion of the femoral component 152 relative to the tibial component 154, the bearing 156 is forced posteriorly, further discussed herein, such that the guide post 244' enters the widened recessed area between the lateral sidewalls 256. As the bearing 156 is forced further posteriorly, further rotational freedom of movement is provided for the bearing 156 relative to the guide post 244', as well as medial to lateral movement during this A-P translation, thereby providing a less constrained knee joint prosthesis 146 with increased flexion. This type of constraint closely mimics an anatomical knee joint. Therefore, by simply changing the style bearing component or opening formed within the bearing 156, varying constraint may be achieved.

Referring back to FIGS. 17 and 18, the articulating bearing surfaces 162 and 164 of the first and second condyles 158 and 160 of the femoral component 152 are shown cooperating with the bearing surfaces 200 and 202 of the floating bearing 156. Each condyle 158 and 160 of the femoral component 152 has a polycentric bearing surface 162 and 164, respectively along the sagittal plane. In this regard, each bearing surface 162 and 164 is defined by a large anterior radius 260 and a smaller posterior/distal radius 262. Point 264 is located just anterior the contact area of the floating bearing 156. Because of this, the bearing surfaces 200 and 202 of the floating bearing 156 are formed with a single radius along the sagittal plane that corresponds to the posterior/distal radius 262. The posterior radius 262 of the condyles 158 and 160 extends up to point 264 cutting into a region of the condyles 158 and 160 to form a pair of opened anterior cavities or regions 268. These opened cavities 268 are positioned above the contact areas of the floating bearing 156 in extension and engage stop regions 270 of the floating bearing 156 during hyper-extension. Correspondingly, the bearing 156 further includes inner regions 272 which engage the inner regions 274 of the condyles 158 and 160 only during hyper-extension. Thus, in extension, the opened anterior cavities 268 are positioned above the stops 270 to eliminate conformity in this region, thereby substantially reducing soft tissue impingement in this area. Contact between the stop region 270 and the anterior cavities 268 only occur during hyper-extension of the knee joint prosthesis 146.

Figure 20A:
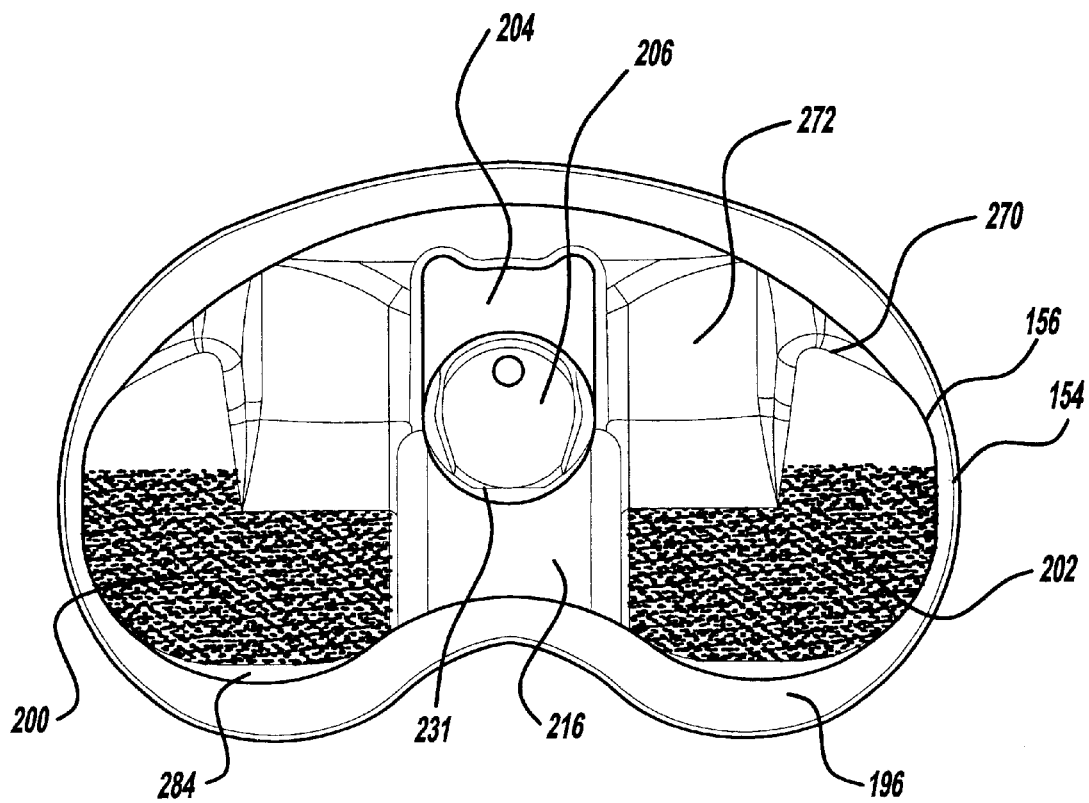
FIGS. 20a–20b are top views of the assembled tibial component and bearing member of FIG. 14 identifying shaded the contact areas in extension and flexion.
Figure 20B:
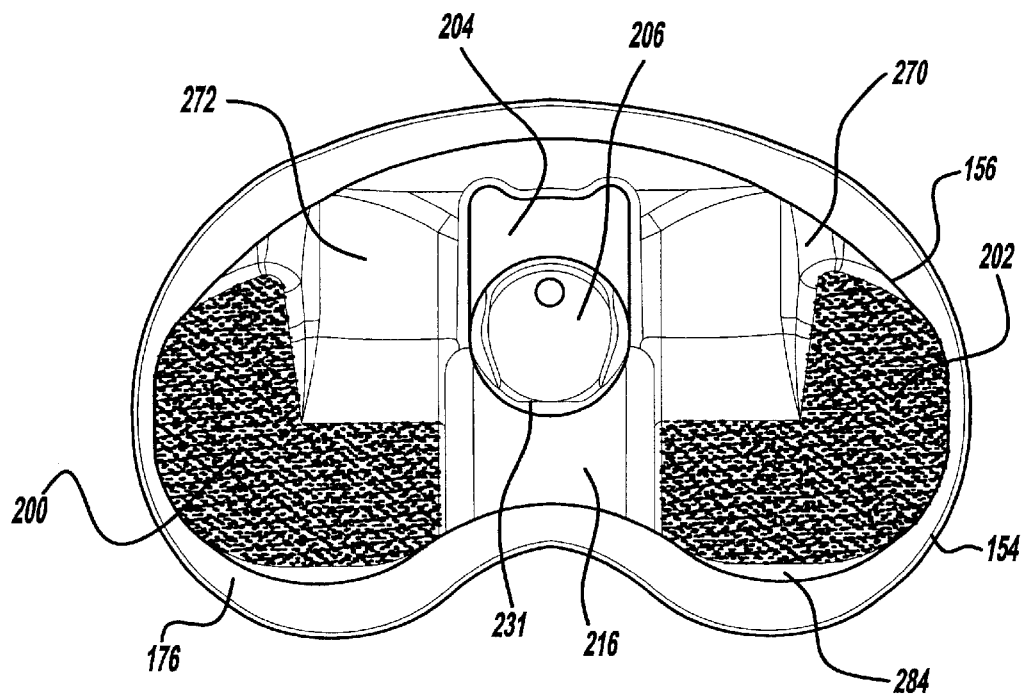

Each bearing surface 162 and 164 of the condyles 158 and 160 are also arcuately shaped with a constant radius 276, along the coronal plane. Correspondingly, the bearing surfaces 200 and 202 of the floating bearing 156 are likewise, formed from a similar constant radius 278 along the coronal plane of the floating bearing 156. Each of the radii 276 and 278 congruently mate with one another to provide a large surface contact area along the coronal plane which increases as flexion increases. In this regard, referring to FIGS. 20a and 20b, the contact area on the floating bearing 156 with the condyle bearing surfaces 162 and 164 in extension are shown shaded in FIG. 20a. It can clearly be observed that a portion of the bearing surfaces 200 and 202 of the floating bearing 156 are in contact with the condyles 158 and 160, except for the stop areas 270 and the inner areas 272, which are only engaged in hyper-extension. In FIG. 20b, the contact area along the floating bearing is shown shaded during flexion of 18° to 110° which illustrates that the contact area increases during flexion to provide further support and less wear of the bearing 156. This surface contact along both the sagittal and coronal planes substantially evenly disburses stresses between the femoral component 152 and the floating bearing 156.

Referring again to FIG. 19, a top view of the assembled tibia component 154, along with the floating bearing 156 is shown. In this regard, the floating bearing 156 has an outer peripheral wall 280 which is substantially concentric with the outer peripheral wall 282 of the tibial tray 182. The outer peripheral wall 280 of the floating bearing 156 also includes a pair of posterior lip extensions 284 which extend out along the bearing surface 198 of the floating bearing 156 (see FIG. 18). This pair of lip extensions 284 eliminates undesirable moment arms as the femoral component 152 moves posterior and rolls up the posterior portion of the center guide post 206 during extreme flexion (see FIG. 23d). In other words, by having the superior articulation or bearing surfaces 200 and 202 extend less posteriorly than the inferior articulation or bearing surface 198, the undesirable moment arm about the floating bearing 156 is eliminated. It should also be noted that a chamfer on the superior surface of the floating bearing 156 may also achieve this or any other configuration as long as the inferior articulation extends posteriorly more than the superior articulation. Therefore, the floating bearing 156 is substantially inhibited from tilting superiorly based upon the moment arms generated upon such flexion. With the floating bearing 156 positioned atop the tibial tray 182 in extension, the guide post 206 is positioned substantially posteriorly of the opening 204, such that the posterior stabilized knee joint prosthesis 146 provides anterior and posterior movement and rotational movement of the floating bearing 156 relative to the tibial component 154. Also the femoral component 152 provides rotational movement along the sagittal plane relative to the floating bearing 156, as well as varus and valgus movement relative to the floating bearing surface 156. It should further be noted that by simply changing the post configuration or the opening configuration, various types of constraints may be easily accommodated.

Figure 23A:
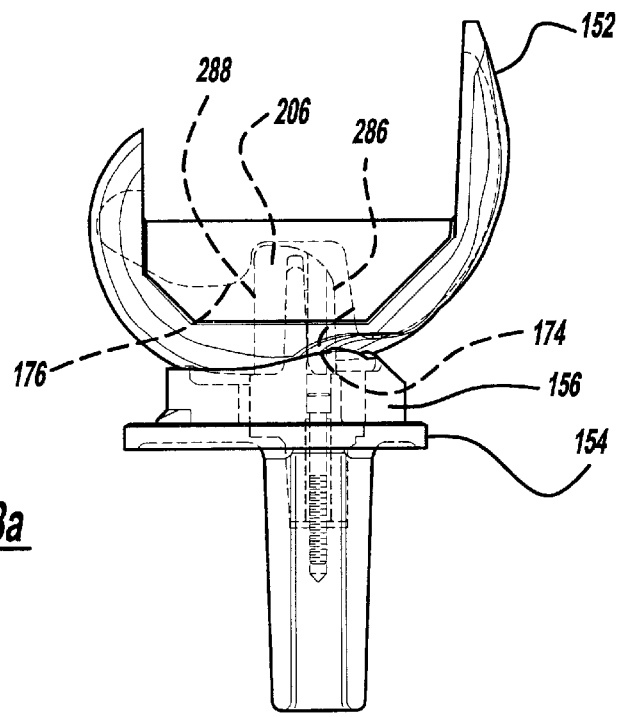
FIGS. 23a–23d are partial sagittal sectional views of the posterior stabilized (PS) knee joint prosthesis, shown in FIG. 14 illustrating four different positions of the femoral component with respect to the tibial component during a range of flexion from full extension to 110° of flexion.
Figure 23B:
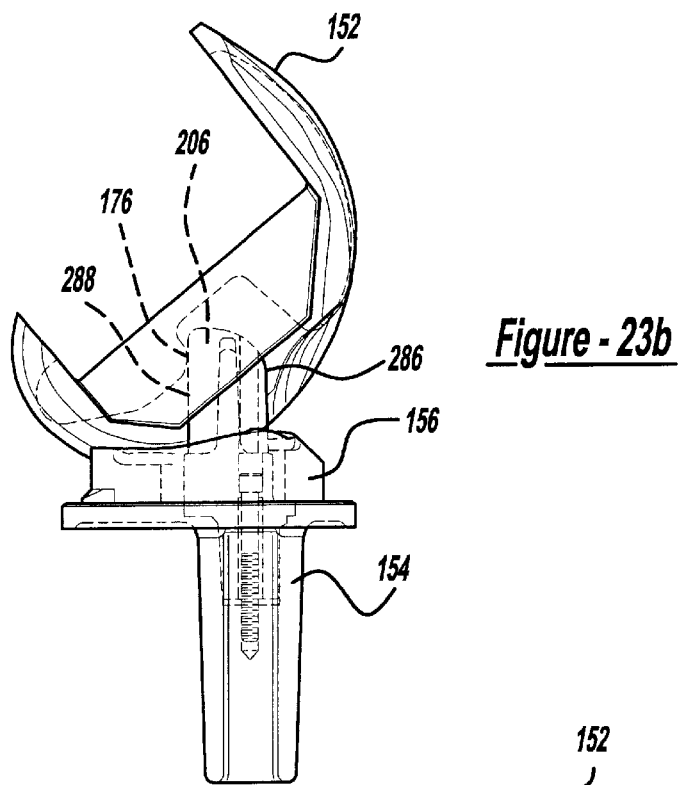
Figure 23C:
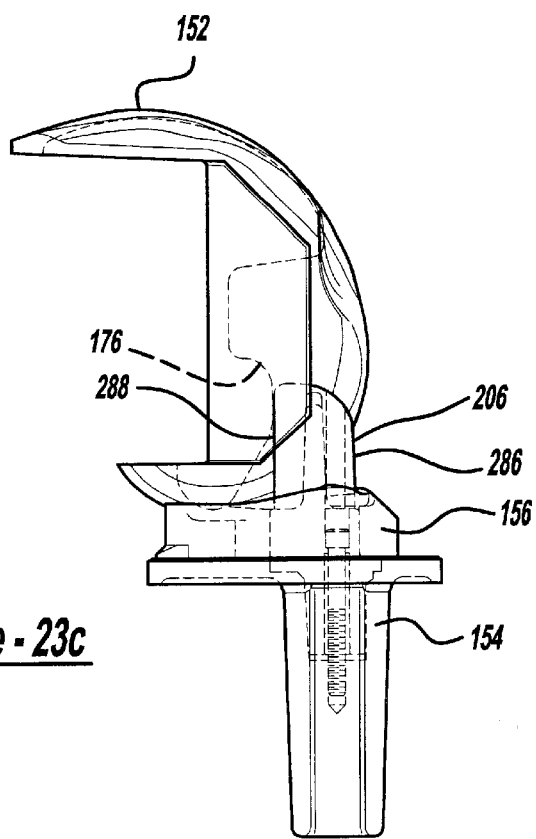
Figure 23D:
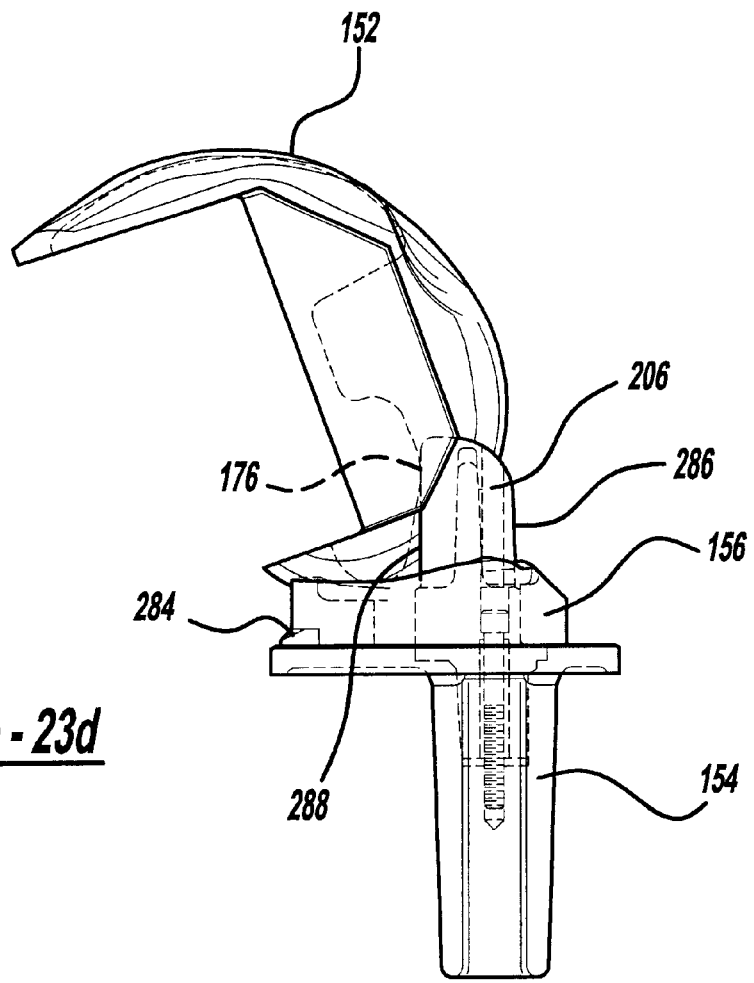

Finally referring to FIGS. 23a–23d, partial sagittal sectional views of the posterior stabilized (PS) knee joint prosthesis 146 illustrating the movement of the femoral component 152 and the floating bearing 156 relative to the tibial component 154 are shown from extension in FIG. 23a to flexion of 110° in FIG. 23d. In FIG. 23a, the posterior stabilized (PS) knee joint prosthesis 146, both anteriorly and posteriorly, is inherently stable at full extension when the patient is standing. In this position, the first and second femoral bearing surfaces 162 and 164 are nested within the first and second tibial bearing surfaces 200 and 202 of the floating bearing 156, respectively. Additionally, the stop portions 270 are not in contact with the anterior cavities 268 in the femoral component 152 to inhibit soft tissue impingement in this region during extension. At 0° flexion, the anterior surface 286 and the posterior surface 288 of the guide post 206 is generally not in engagement with the anterior sidewall 212 or the posterior sidewall 210 of the opening 204 or with the posterior cam 176 or the anterior wall 174 of the inner condylar portion 166. Should the knee joint prosthesis 146 undergo a large hyper-extension (approximately 10°), the anterior surface 286 of the guide post 206 would engage the anterior sidewall 174 of the inner condylar portion 166. The pair of anterior cavities 268 of the femoral component 152 would also engage the stops 270 of the bearing 156, while the inner condylar bearing surfaces 274 would engage the inner surfaces 272 of the floating bearing 156. This engagement will avoid posterior dislocation of the femoral component 152 relative to the tibial component 154.

As flexion of the knee joint prosthesis 146 occurs, the posterior cam 176 will generally engage the posterior side 288 of the post 206 at about 40° of flexion, as shown in FIG. 23b. Before this engagement, the femoral component 152, the tibial component 154 and the floating bearing 156 is generally most unrestricted, such that the femoral component 152 is permitted to translate in the sagittal plane along with the floating bearing 156 relative to the tibial component 154. Upon engagement of the cam 176 relative to the posterior side 288 of the post 206, the floating bearing 156 rolls back posteriorly relative to the tibial tray 182. This causes the floating bearing 156, having bearing surface 198, to slide relative to the bearing surface 196 of the tibial tray 182. While this forced rollback of the floating bearing 156 is occurring, the bearing surfaces 162 and 164 of the femoral component 152 are nestingly received within the bearing surfaces 200 and 202 of the floating bearing 156 (shown highlighted in FIG. 20b).

As flexion continues to about 90°, shown in FIG. 23c, a forced rollback of the floating bearing 156 relative to the tibial tray 182 continues to occur while the contact area between the femoral component and floating bearing increases as shown in FIG. 20b. Upon flexion reaching about 110°, the femoral component 156 moves posteriorly and rolls up upon the posterior side 288 of the guide post 206 reducing the contact area between the femoral component 152 and the bearing 156. The posterior lip extension 284 prevent the floating bearing 156 from flipping up or tipping superiorly during this phase of flexion by reducing the moment arm about the contact point of the posterior cam 176 to the contact surface between the femoral component 152 and the floating bearing 156.

As can be observed from FIGS. 23a–23d, forced rollback provided by the engagement of the fixed modular guide post 206 with the cam 176 provides a surface contact area between the femoral component 152 and the floating bearing 156 which increases as flexion increases (see FIGS. 20a–20b), until extreme flexion (i.e., $\geq 110°$). Moreover, by providing engagement of the cam 176 with the guide post 206 at about 40° of flexion, wear on the guide post 206 is substantially reduced because the post/cam contact occurs after the loading phase of normal gait. In addition, by delaying the cam engagement until after the loading phase of gait, the cam 176 contacts the guide post 206 closer to the tibial/femoral articulation or lower along the guide post 206. This lower contact point reduces the moment arm on the guide post 206, and therefore, the stresses on the guide post 206. It should further be noted that the guide post 206 maintains the position of the bearing 156 from 0° to 40° of flexion since tibial or femoral congruency is maintained and the bearing cannot slide forward with the posterior surface of the opening, engaging the posterior side 288 of the post 206. Finally, since the highest load placed on the quad mechanism or muscle occurs during stair climbing or after 40° of flexion and the cam 176 engages the post 206 at 40°, this forces the rollback to maintain at least physiological rollback and extension moment arm values, thereby enabling patients to perform high demand activities without altering their gait or posture to compensate for a compromised quad mechanism.

The foregoing discussion discloses and describes merely exemplary embodiments of the present invention. One skilled in the art will readily recognize from such, discussion, and from the accompanying drawings and claims, that various changes, modifications and variations can be made therein without departing from the spirit and scope of the invention as defined in the following claims.

What is claimed is:

1. A knee joint prosthesis for replacing an articulating knee portion of a femur and a tibia, said knee joint prosthesis comprising:

a femoral component having an engagement member, a first femoral bearing surface and a second femoral bearing surface;

a tibial component having a tibial bearing surface;

a guide post extending from said tibial component and operable to be engaged by said engagement member of said femoral component; and a bearing member having a first bearing surface operable to articulate with said first femoral bearing surface, a second bearing surface operable to articulate with said second femoral bearing surface, and a third bearing surface operable to articulate with said tibial bearing surface, said bearing member further having an outer peripheral wall that includes a pair of posterior lip extensions that extend out along said third bearing surface so that said third bearing surface extends further posteriorly than said first and second bearing surfaces, wherein said bearing member is substantially inhibited from dislocating upon flexion of said knee joint prosthesis.

2. The knee joint prosthesis as defined in claim 1 wherein said guide post is removably secured to said tibial component.

3. A knee joint prosthesis for replacing an articulating knee portion of a femur and a tibia, said knee joint prosthesis comprising:

a femoral component having an engagement member, a first femoral bearing surface and a second femoral bearing surface;

a tibial component having a tibial bearing surface;

a guide post removably secured to and extending from said tibial component and operable to be engaged by said engagement member of said femoral component, said guide post includes a retention mechanism operable to retain and inhibit a connecting bolt from separating from said guide post; and a bearing member having a first bearing surface operable to articulate with said first femoral bearing surface, a second bearing surface operable to articulate with said second femoral bearing surface, and a third bearing surface operable to articulate with said tibial bearing surface, said third bearing surface extending further posteriorly than said first and second bearing surfaces, wherein said bearing member is substantially inhibited from dislocating upon flexion of said knee joint prosthesis.

4. The knee joint prosthesis as defined in claim 3 wherein said retention mechanism is defined by a stepped shoulder within a bore passing through said guide post.

5. A knee joint prosthesis for replacing an articulating knee portion of a femur and a tibia, said knee joint prosthesis comprising:

a femoral component having an engagement member, a first femoral bearing surface and a second femoral bearing surface;

a tibial component having a tibial bearing surface;

a guide post extending from said tibial component and operable to be engaged by said engagement member of said femoral component, said guide post includes a first guide portion having a first shape and a second guide portion having a second shape, said first shape being different from said second shape; and a bearing member having a first bearing surface operable to articulate with said first femoral bearing surface, a second bearing surface operable to articulate with said second femoral bearing surface, and a third bearing surface operable to articulate with said tibial bearing surface, said third bearing surface extending further posteriorly than said first and second bearing surfaces, wherein said bearing member is substantially inhibited from dislocating upon flexion of said knee joint prosthesis, wherein said first guide portion is operable to engage said bearing member to control the relative movement of said bearing member and said second guide portion is operable to engage said femoral component to control the relative movement of said femoral component.

6. The knee joint prosthesis as defined in claim 5 wherein said first guide portion includes a pair of annularly positioned arcuate lobes operable to limit rotational movement of said bearing member relative to said tibial component.

7. The knee joint prosthesis as defined in claim 6 wherein said bearing member defines an opening passing through said bearing member, said opening defined by an anterior sidewall, a posterior sidewall, and a pair of lateral sidewalls that widen said opening anteriorly.

8. A knee joint prosthesis for replacing an articulating knee portion of a femur and a tibia, said knee joint prosthesis comprising:

a femoral component having an engagement member, a first femoral bearing surface and a second femoral bearing surface;

a tibial component having a tibial bearing surface;

a guide post extending from said tibial component and operable to be engaged by said engagement member of said femoral component; and a bearing member having a first bearing surface operable to articulate with said first femoral bearing surface, a second bearing surface operable to articulate with said second femoral bearing surface and a third bearing surface operable to articulate with said tibial bearing surface, said bearing member further defining an opening passing through said bearing member and operable to receive said guide post through said opening in said bearing member, wherein said guide post and said opening are configured to substantially inhibit rotational movement of said bearing member relative to said tibial component in extension while providing greater rotational freedom of said bearing member relative to said tibial component as flexion of said knee joint prosthesis increases.

9. The knee joint prosthesis as defined in claim 8 wherein said opening is defined by an anterior sidewall, a posterior sidewall and a pair of lateral sidewalls, said pair of lateral sidewalls widening said opening anteriorly to provide for a larger anterior opening area, thereby providing less constraint of the knee joint prosthesis as flexion increases.

10. The knee joint prosthesis as defined in claim 8 wherein said guide post is removably secured to said tibial component.

11. The knee joint prosthesis as defined in claim 10 wherein said guide post further includes a retention mechanism operable to retain and inhibit a connecting bolt from separating from said guide post.

12. The knee joint prosthesis as defined in claim 11 wherein said retention mechanism is defined by a stepped shoulder within a bore passing through said guide post.

13. The knee joint prosthesis as defined in claim 12 wherein said guide post includes a first guide portion having a first shape and a second guide portion having a second shape, said first shape being different from said second shape, said first guide portion operable to engage said bearing member to control the relative movement of said bearing member and said second guide portion operable to engage said femoral component to control the relative movement of said femoral component.

14. The knee joint prosthesis as defined in claim 13 wherein said first guide portion includes a pair of annularly positioned arcuate lobes operable to limit rotational movement of said bearing member relative to said tibial component.

15. The knee joint prosthesis as defined in claim 8 wherein said bearing member further includes a posterior lip extension extending said third bearing surface posteriorly.

16. The knee joint prosthesis as defined in claim 8 wherein said tibial component includes a tibial plateau and a tibial stem, said tibial stem having a substantially I-beam cross section at a distal tip of said tibial stem.

17. A knee joint prosthesis for replacing an articulating portion of a femur and a tibia, said knee joint prosthesis comprising:

a femoral component having an engagement member, a first femoral bearing surface and a second femoral bearing surface;

a tibial component having a tibial bearing surface;

a guide post extending from said tibial component and operable to be engaged by said engagement member of said femoral component, said guide post including a pair of lobes extending from said guide post; and a bearing member having a first bearing surface operable to articulate with said first femoral bearing surface, a second bearing surface operable to articulate with said second femoral bearing surface, and a third bearing surface operable to articulate with said tibial bearing surface, said bearing member further defining an opening passing through said bearing member, wherein said pair of lobes are operable to engage a sidewall defining said opening to control rotational movement of said bearing member relative to said tibial component.

18. The knee joint prosthesis as defined in claim 17 wherein said guide post is removably secured to said tibial component.

19. The knee joint prosthesis as defined in claim 18 wherein said guide post further includes a retention mechanism operable to retain and inhibit a connecting bolt from separating from said guide post.

20. The knee joint prosthesis as defined in claim 17 wherein said pair of lobes extend anteriorly.

* * * * *

UNITED STATES PATENT AND TRADEMARK OFFICE
CERTIFICATE OF CORRECTION

PATENT NO.   : 6,413,279 B1
DATED        : July 2, 2002
INVENTOR(S)  : Robert Metzger et al.

It is certified that error appears in the above-identified patent and that said Letters Patent is hereby corrected as shown below:

<u>Title page,</u>
Item [56], References Cited, OTHER PUBLICATIONS, "Track Knee System" reference, "Lawrency" should be -- Lawrence --.

<u>Column 1,</u>
Line 61, "cylinderally" should be -- cylindrically --.

<u>Column 4,</u>
Line 67, "shaded the" should be -- the shaded --.

<u>Column 11,</u>
Line 63, "tibial" should be -- tibia --.

Signed and Sealed this

Sixteenth Day of December, 2003

JAMES E. ROGAN
*Director of the United States Patent and Trademark Office*